United States Patent
Khuri-Yakub et al.

(10) Patent No.: US 11,260,248 B2
(45) Date of Patent: Mar. 1, 2022

(54) DETECTION, LOCALIZATION, AND/OR SUPPRESSION OF NEURAL ACTIVITY USING ACOUSTIC WAVES AND/OR ULTRASOUND

(71) Applicant: The Board of Trustees of the Leland Stanford Junior University, Stanford, CA (US)

(72) Inventors: Butrus T. Khuri-Yakub, Palo Alto, CA (US); Kamyar Firouzi, Palo Alto, CA (US); George Quintin Stedman, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 17/269,503

(22) PCT Filed: Sep. 26, 2019

(86) PCT No.: PCT/US2019/053097
§ 371 (c)(1),
(2) Date: Feb. 18, 2021

(87) PCT Pub. No.: WO2020/069084
PCT Pub. Date: Apr. 2, 2020

(65) Prior Publication Data
US 2021/0260411 A1   Aug. 26, 2021

Related U.S. Application Data

(60) Provisional application No. 62/738,812, filed on Sep. 28, 2018.

(51) Int. Cl.
*A61N 7/00* (2006.01)
*G16H 20/40* (2018.01)
(Continued)

(52) U.S. Cl.
CPC .............. *A61N 7/00* (2013.01); *A61B 5/4064* (2013.01); *A61B 5/4094* (2013.01); *A61B 7/001* (2013.01);
(Continued)

(58) Field of Classification Search
CPC .............. A61N 7/00; A61N 2007/0052; A61N 2007/0026; A61B 7/00; A61B 7/001;
(Continued)

(56) References Cited

U.S. PATENT DOCUMENTS

| | | | |
|---|---|---|---|
| 2005/0203366 A1 | 9/2005 | Donoghue et al. | |
| 2007/0073150 A1* | 3/2007 | Gopalsami | A61B 8/4472 600/438 |

(Continued)

FOREIGN PATENT DOCUMENTS

| | | | |
|---|---|---|---|
| GB | 2479705 | 10/2011 | |
| GB | 2479705 A | * 10/2011 | ........... A61B 5/4094 |

OTHER PUBLICATIONS

Min, Byoung-Kyong, et al. "Focused ultrasound-mediated suppression of chemically-induced acute epileptic EEG activity." BMC neuroscience 12.1 (2011): 1-12. (Year: 2011).*

(Continued)

*Primary Examiner* — Sean D Mattson
(74) *Attorney, Agent, or Firm* — Knobbe, Martens, Olson & Bear, LLP

(57) ABSTRACT

Systems and methods are disclosed related to using acoustic waves to detect neural activity in a brain and/or localize the neural activity in the brain. Sensors positioned outside of a skull encasing the brain can detect acoustic waves associated with the neural activity in the brain. From output signals of the sensors, a particular type of neural activity (e.g., a seizure) can be detected. A location of the neural activity can be determined based on outputs of the sensors. In some (Continued)

embodiments, the ultrasound energy can be applied to the location of the neural activity in response to detecting the neural activity.

20 Claims, 19 Drawing Sheets

(51) Int. Cl.
| | |
|---|---|
| *G16H 40/67* | (2018.01) |
| *G16H 50/20* | (2018.01) |
| *G06N 20/00* | (2019.01) |
| *A61B 5/00* | (2006.01) |
| *A61B 7/00* | (2006.01) |
| *A61B 8/08* | (2006.01) |
| *A61B 8/00* | (2006.01) |
| *G10K 11/34* | (2006.01) |
| *G10L 25/66* | (2013.01) |

(52) U.S. Cl.
CPC .......... *A61B 8/0808* (2013.01); *A61B 8/4209* (2013.01); *A61B 8/485* (2013.01); *G06N 20/00* (2019.01); *G10K 11/341* (2013.01); *G10L 25/66* (2013.01); *G16H 20/40* (2018.01); *G16H 40/67* (2018.01); *G16H 50/20* (2018.01); *A61N 2007/0026* (2013.01); *A61N 2007/0052* (2013.01)

(58) Field of Classification Search
CPC ..... A61B 8/4209; A61B 8/0808; A61B 8/485; G16H 20/40; G16H 50/20; G16H 40/67; G10L 25/66; G06N 20/00; G10K 11/341
See application file for complete search history.

(56) References Cited

U.S. PATENT DOCUMENTS

| | | | | |
|---|---|---|---|---|
| 2010/0076520 | A1* | 3/2010 | Miller, III | ............ H04R 25/606 607/57 |
| 2012/0283604 | A1* | 11/2012 | Mishelevich | .......... A61N 2/006 601/2 |
| 2012/0289869 | A1* | 11/2012 | Tyler | ...................... A61B 5/369 601/2 |
| 2014/0058292 | A1* | 2/2014 | Alford | ..................... A61N 7/00 601/2 |
| 2015/0208934 | A1* | 7/2015 | Sztrubel | ............... A61B 5/4893 600/547 |
| 2016/0220850 | A1 | 8/2016 | Tyler | |
| 2018/0280735 | A1 | 10/2018 | Khuri-Yakub et al. | |

OTHER PUBLICATIONS

Vanleer, Ann C., et al. "Millimeter-scale epileptiform spike propagation patterns and their relationship to seizures." Journal of neural engineering 13.2 (2016): 026015. (Year: 2016).*

Vanleer, Ann et al., "Millimeter-scale epileptiform spike propagation patterns and their relationship to seizures," J Neural Eng., Apr. 2016.

International Search Report dated Dec. 10, 2019 for International Patent Application No. PCT/US1953097.

Written Opinion dated Dec. 10, 2019 for International Patent Application No. PCT/US1953097.

K. Firouzi, A. Nikoozadeh and B. T. Khuri-Yakub, "Lamb Wave Multitouch Ultrasonic Touchscreen," IEEE Trans. Ultrason., Ferroelect., Freq. Control, vol. 63, No. 12, pp. 2174-2186, 2016.

K. Firouzi and B. T. Khuri-Yakub, "A Learning Method for Localization of Objects in Reverberant Domains with Limited Measurements," J. Acoust. Soc. Am., vol. 141, No. 1, pp. 104-115, 2017.

K. Firouzi, P. Ghanouni, B. T. Khuri-Yakub, "Efficient Transcranial Ultrasound Delivery Via Excitation of Lamb Waves: Concept and Preliminary Results", 2017.

K Iwasa, I Tasaki, RC Gibbons, "Swelling of nerve fibers associated with action potentials," Science, vol. 210, Issue 4467, pp. 338-339, 1980.

V. Colucci, G. Strichartz, F. Jolesz, N. Vykhodtseva, K. Hynynen, "Focused Ultrasound Effects on Nerve Action Potential in vitro," Ultrasound Med. Biol., vol. 35, Issue 10, pp. 1737-1747, Oct. 2009.

* cited by examiner

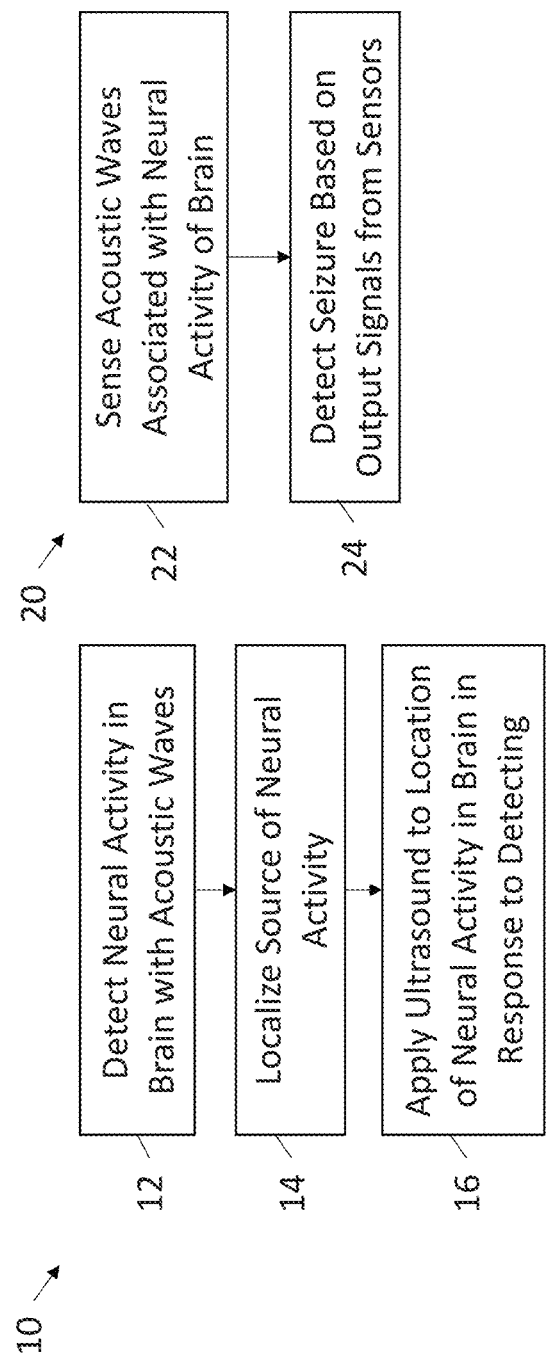

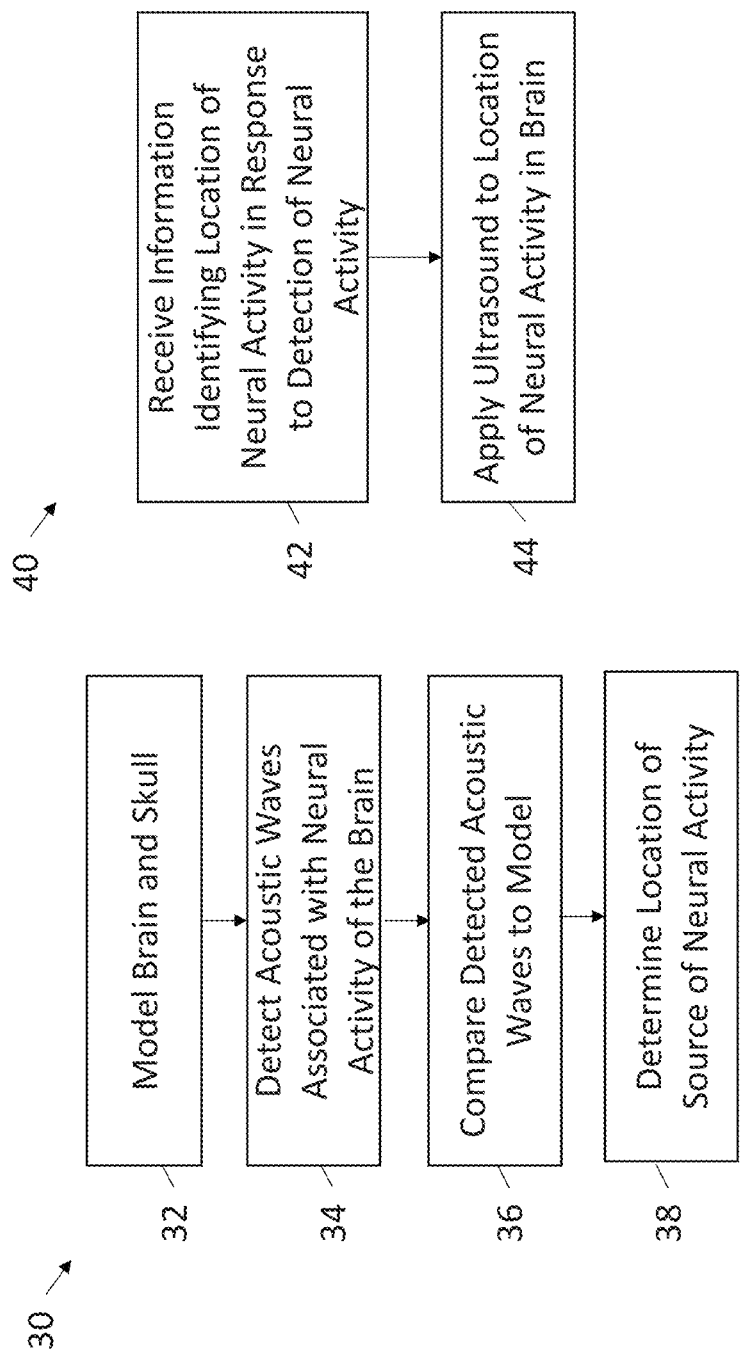

3D Simulation with Hemispherical Skull

Point 1 (@origin)
Point 2 (@45°)
Input Normal Surface Velocity (1 m/s), Radius 1 mm Measurement Points of 16 Distributed Measurement Points Skull Radius is 10 cm

DETECTION, LOCALIZATION, AND/OR SUPPRESSION OF NEURAL ACTIVITY USING ACOUSTIC WAVES AND/OR ULTRASOUND

CROSS REFERENCE TO PRIORITY APPLICATION

This application claims the benefit of priority of U.S. Provisional Patent Application No. 62/738,812, filed Sep. 28, 2019 and titled "DETECTION, LOCALIZATION, AND/OR SUPPRESSION OF BRAIN SWELLING USING ACOUSTIC WAVES AND/OR ULTRASOUND," the disclosure of which is hereby incorporated by reference in its entirely.

BACKGROUND

Technological Field

The disclosed technology relates to using acoustic waves to detect and/or localize and/or suppress brain swelling.

Description of Related Technology

Epilepsy is characterized by epileptic seizures. Epileptic seizures are episodes that can involve vigorous shaking. Such seizures tend to recur and there may be no known immediate underlying cause of such seizures.

There are various non-invasive technologies for detecting epileptic seizures. High temporal resolution and high spatial resolution can be desired for properly diagnosing epilepsy. However, there are technical challenges to achieving both high temporal resolution together with high spatial resolution.

SUMMARY OF CERTAIN INVENTIVE ASPECTS

The innovations described in the claims each have several aspects, no single one of which is solely responsible for its desirable attributes. Without limiting the scope of the claims, some prominent features of this disclosure will now be briefly described.

One aspect of the disclosed technology is a system for detecting seizures. The system includes sensors and a processor in communication with the sensors. The sensors are positioned outside of a skull encasing a brain. The sensors are configured to detect acoustic waves associated with neural activity in the brain. The processor is configured to process output signals from the sensors and detect a seizure based on the output signals from the sensors.

The processor can localize a source of the seizure with resolution on the order of millimeters. This localization of the source of the seizure can involve machine learning techniques. The system can include ultrasonic transducers in communication with the processor. The processor can control the ultrasonic transducers to apply ultrasound to the source of the seizure in response to detecting the seizure. The ultrasound can have a frequency in a range from 0.5 megahertz to 5 megahertz. The processor can control the ultrasonic transducers to apply the ultrasound within a millisecond time range from receiving outputs of the sensors.

The sensors can include any suitable sensors. The sensors can include acoustic transducers. The sensors can include accelerometers. The sensors can include optical sound sensors.

The sensors can be integrated on a helmet for the skull. The processor can also be integrated on the helmet. Alternatively, the sensors can be configured for implantation between the skull and a scalp.

The acoustic waves can have wavelengths on an order of a meter.

Another aspect of this disclosure is a method of detecting seizures from acoustic waves. The method includes sensing, with sensors positioned outside of a skull encasing a brain, acoustic waves associated with neural activity of the brain; and detecting, with a processor in communication with the sensors, a seizure based on output signals of the sensors.

The sensors can include acoustic transducers. Alternatively or additionally, the sensors can include accelerometers.

The acoustic waves can include shear waves. The acoustic waves can include compressional waves. The compressional waves can have a wavelength on an order of a meter. The acoustic waves can include shear waves and compressional waves.

The method can include localizing a source of the seizure with resolution on the order of millimeters. The localizing can include applying machine learning techniques. The method can include applying ultrasound energy to the source of the seizure in response to detecting the seizure. The ultrasound energy can have a frequency in a range from 0.5 megahertz to 5 megahertz. Applying the ultrasound energy can be performed within a millisecond time range from receiving outputs of the sensors.

Another aspect of this disclosure is a method of detecting and suppressing seizures. The method includes sensing, with sensors positioned outside of a skull encasing a brain, acoustic waves associated with neural activity of the brain at a plurality of locations; comparing, with a processor in communication with the sensors, data derived using the sensors with a model associated with the skull; based on the comparing, determining a location of the neural activity of the brain with a resolution on the order of millimeters; and applying, using one or more ultrasonic transducers, ultrasound energy to the location of the neural activity in the brain through the skull within a millisecond time range from the determining.

Another aspect of this disclosure is a method of localizing a source of a seizure. The method includes sensing, with sensors positioned outside of a skull encasing a brain, acoustic waves at a plurality of locations; and determining, with a processor in communication with the sensors, a location of a source of the seizure with a resolution on the order of millimeters based on the outputs of the sensors.

The determining can include comparing data from the sensors with a model associated with the skull to thereby determine the location of the source. The method can further includes generating the model using machine learning techniques.

The sensing can include sensing shear waves. Alternatively or additionally, the sensing can include sensing compressional waves.

The method can include applying focused ultrasound energy to the location of the source in response to the determining.

The sensors can include acoustic transducers. The sensors can be integrated with a helmet. Alternatively, the sensors can be positioned between the skull and a scalp.

Another aspect of this disclosure is a system for localizing a source of a seizure in the brain. The system includes sensors positioned outside of a skull encasing a brain and a processor in communication with the sensors. The sensors are configured to detect acoustic waves at a plurality of locations. The processor is configured to determine a location of a source of the seizure with a resolution on the order of millimeters based on the outputs of the sensors.

The processor can compare data from the sensors with a model associated with the skull to thereby determine the location of the source. The processor can generate the model using machine learning techniques.

The sensors can be configured to sense shear waves. The sensors can be configured to sense compressional waves.

The system can include ultrasonic transducers configured to apply focused ultrasound energy to the location of the source in response to the processor determining the location of the source.

The system can include a helmet integrated with the sensors.

Another aspect of this disclosure is a method of suppressing neural activity in a brain encased by a skull. The method includes receiving information associated with the neural activity in the brain, the information identifying a location of the neural activity in the brain; and applying, using one or more ultrasonic transducers, an ultrasound signal to the location of the neural activity in the brain through the skull in response to the receiving to thereby suppress the neural activity.

The neural activity can be associated with a seizure. The information identifying the location of the neural activity can have a resolution on the order of a millimeter.

The applying can be performed within millisecond time range from sensors detecting the neural activity.

The ultrasound signal can have a frequency in a range from 0.5 megahertz to 1 megahertz.

Another aspect of this disclosure is a system for suppressing neural activity in a brain encased by a skull. The system includes ultrasonic transducers and a processor. The ultrasonic transducers are configured to apply ultrasound through the skull to a location of the brain. The processor is configured to detect neural activity in the brain, identify a location of the neural activity in the brain with a resolution on an order of a millimeter, and control the ultrasonic transducers to apply the ultrasound to the location in response to detecting the neural activity.

The system can include a helmet. The ultrasonic transducers can be integrated with the helmet.

The processor can be configured to cause the ultrasonic transducers to apply the ultrasound to the location within a millisecond time range from detecting the neural activity.

The ultrasound can have a frequency in a range from 0.5 megahertz to 5 megahertz.

The neural activity can be associated with a seizure.

The system can include sensors arranged to detect acoustic waves associated with the neural activity, in which the processor is configured to detect the neural activity based on output signals from the sensors.

Any of the above aspects can be combined with each other as suitable. The present disclosure contemplates combining one or more features of each of the above aspects in each and every suitable combination.

For purposes of summarizing the disclosure, certain aspects, advantages and novel features of the innovations have been described herein. It is to be understood that not necessarily all such advantages may be achieved in accordance with any particular embodiment. Thus, the innovations may be embodied or carried out in a manner that achieves or optimizes one advantage or group of advantages as taught herein without necessarily achieving other advantages as may be taught or suggested herein.

BRIEF DESCRIPTION OF THE DRAWINGS

FIG. 1 is a flow diagram of a method of detecting, localizing and suppressing neural activity in the brain according to an embodiment.

FIG. 2 is a flow diagram of a method of detecting neural activity in the brain according to an embodiment.

FIG. 3 is a flow diagram of a method of localizing a source of neural activity in the brain according to an embodiment.

FIG. 4 is a flow diagram of a method of suppressing neural activity in the brain according to an embodiment.

DETAILED DESCRIPTION OF CERTAIN EMBODIMENTS

Figure 5:
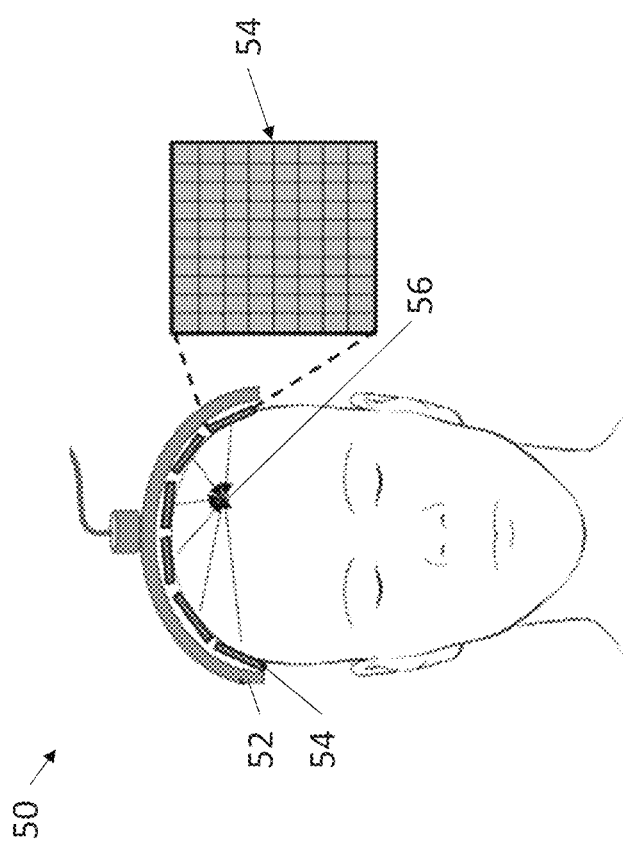
FIG. 5 illustrates a system for detecting and suppressing epileptic seizures positioned relative to a human head according to an embodiment.

The following description of certain embodiments presents various descriptions of specific embodiments. However, the innovations described herein can be embodied in a multitude of different ways, for example, as defined and covered by the claims. In this description, reference is made to the drawings where like reference numerals can indicate identical or functionally similar elements. It will be understood that elements illustrated in the figures are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings. Headings provided herein are for convenience only and do not necessarily affect the scope or meaning of the claims.

For detection of epileptic seizures, non-invasive technology includes an electroencephalogram (EEG), functional magnetic resonance imaging (MRI)/computed tomography (CT) scans, and magnetoencephalography (MEG). For proper diagnosis or detection of epilepsy, both high temporal resolution and spatial resolution can be desired. EEG has a poor spatial resolution. Functional MRI and CT can be used for detection of epileptic events. They provide good spatial resolution. However, they have poor temporal resolution. Moreover, they are expensive and not portable. Despite limited spatial resolution, EEG continues to be a valuable tool for research and diagnosis. It is one of the few mobile techniques available and offers millisecond-range temporal resolution which is not currently possible with CT, positron emission tomography (PET), or MRI. Some treatments for epilepsy include surgery where either neurostimulator electrodes are implanted in the brain or a section of the brain is removed.

Aspects of this disclosure relate to detection, localization, and/or suppression of an epileptic seizure and/or other neural activity in the brain. An acoustic wave from a seizure can be detected using acoustic transducers and/or any other suitable sensor. An acoustic transducer that can generate and/or detect an acoustic signal having a frequency of at least 20 kilohertz (kHz) can be referred to as an ultrasonic transducer. The coupling to a skull can provide a unique texture into the acoustic waves. This can enable localization of the source of the seizure within a few millimeters (mm) even though the wave length of a pressure wave is in the meter range. The disclosed technology can provide good temporal resolution and spatial resolution in detecting a seizure and/or other neural activity in the brain. In response to detecting a seizure at a particular location, ultrasound energy can be applied to the particular location to suppress action potential firings to thereby blunt a seizure.

In embodiments disclosed herein, sensors (e.g., an array of acoustic transducers and/or accelerometers) are positioned in a helmet over the head of a person. The array of sensors can be arranged to detect an epileptic event at relatively low frequencies (e.g., in the kHz range). The epileptic event can be localized with millimeter resolution. In response to detecting and localizing the epileptic event, ultrasonic transducers can suppress the epileptic event by applying ultrasound energy at relatively high frequencies (e.g., 100s of kHz) using a method to beamform a transmitted pressure at the location of the event.

The technology disclosed herein can achieve good spatial resolution and good temporal resolution for detecting neural activity in a brain. The disclosed techniques for detection, localization, and/or suppression of epileptic seizure are non-invasive. Accordingly, the disclosed technology provides a non-invasive treatment that can suppress a seizure in time so that severe consequences of the seizure can be reduced, minimized, and/or eliminated.

Epilepsy

Epilepsy is a group of neurological disorders characterized by epileptic seizures. Epileptic seizures are episodes that can vary from brief and nearly undetectable periods to relatively long periods of vigorous shaking. These episodes can result in physical injuries, including occasionally broken bones. In epilepsy, seizures tend to recur and have no immediate underlying cause.

The cause of most cases of epilepsy is unknown. Some cases occur as the result of brain injury, stroke, brain tumors, infections of the brain, and/or birth defects through a process known as epileptogenesis. Epileptic seizures are thought to be the result of excessive and abnormal neuronal activity in the cortex of the brain. The diagnosis typically involves ruling out other conditions that might cause similar symptoms, such as fainting, and determining if another cause of seizures is present, such as alcohol withdrawal or electrolyte problems. This may be partly done by imaging the brain and performing blood tests. Epilepsy can often be confirmed with an electroencephalogram (EEG).

As of 2015, about 39 million people were thought to have epilepsy. Nearly 80% of cases of epilepsy occur in the developing world. In 2015, epilepsy resulted in 125,000 deaths up from 112,000 deaths in 1990. Epilepsy is more common in older people. In the developed world, the onset of new cases occurs most frequently in babies and the elderly. In the developing world, onset is more common in older children and young adults, due to differences in the frequency of the underlying causes. About 5-10% of people are estimated to have an unprovoked seizure by the age of 80, and the chance of experiencing a second seizure is thought to be between 40 and 50%. In many areas of the world, those with epilepsy either have restrictions placed on their ability to drive or are not permitted to drive until they are free of seizures for a specific length of time.

The diagnosis of epilepsy is typically made based on observation of the seizure onset and the underlying cause. An EEG to look for abnormal patterns of brain waves and neuroimaging (CT scan and/or MRI) to look at the structure of the brain can also be part of the workup. While figuring out a specific epileptic syndrome is often attempted, it is not always possible. Video and EEG monitoring may be useful in difficult cases.

An EEG can assist in showing brain activity suggestive of an increased risk of seizures. It is typically only recommended for those who are likely to have had an epileptic seizure on the basis of symptoms. In the diagnosis of epilepsy, electroencephalography may help distinguish the type of seizure or syndrome present.

Diagnostic imaging by CT scan and MRI is typically recommended after a first non-febrile seizure to detect structural problems in and/or around the brain. MRI is generally a better imaging test except when bleeding is suspected, for which CT is more sensitive and more easily available. If someone attends the emergency room with a seizure but returns to normal quickly, imaging tests may be done at a later point.

Wristbands and/or bracelets denoting their condition are occasionally worn by epileptics should they need medical assistance. Epilepsy can be treated with daily medication once a second seizure has occurred, while medication may be started after the first seizure in those at high risk for subsequent seizures. Diet, alternative medicine, and people's self-management of their condition (such as avoidance therapy consisting of minimizing or eliminating triggers) may be useful. In drug-resistant cases or cases experiencing severe side effects, different and harsher management options may be considered including the implantation of a neurostimulator or neurosurgery.

Epilepsy surgery may be an option for people with focal seizures that remain a problem despite other treatments. These other treatments typically include at least a trial of two or three medications. The goal of surgery is total control of seizures and this may be achieved in about 60-70% of cases. Common procedures include cutting out the hippocampus via an anterior temporal lobe resection, removal of tumors, and removing parts of the neocortex. Some procedures such as a corpus colostomy are attempted in an effort to decrease the number of seizures rather than cure the condition. Following surgery, medications may be slowly withdrawn in many cases.

Neurostimulation may be another option in those who are not candidates for surgery. Three types of neurostimulation have been shown to be effective in those who do not respond to medications: vagus nerve stimulation, anterior thalamic stimulation, and closed-loop responsive stimulation.

Epilepsy cannot usually be cured, unless surgery is performed. However, the outcome of surgery can lead to unexpected harsh outcomes such as loss of functionality of certain abilities such as speech, control over movements, etc. In the developing world, 75% of people are thought to be either untreated or not appropriately treated for epilepsy. In Africa, it is estimated that 90% of people with epilepsy do not get treatment. This is partly related to appropriate medications not being available and/or being too expensive.

People with epilepsy are at an increased risk of death. This increase is between 1.6 and 4.1-fold greater than that of the general population and is often related to: the underlying cause of the seizures, status epilepticus, suicide, trauma, and sudden unexpected death in epilepsy (SUDEP). Death from status epilepticus is primarily due to an underlying problem rather than missing doses of medications. The risk of suicide is between two and six times higher in those with epilepsy. The cause of this is unclear. The greatest increase in mortality from epilepsy is among the elderly. Those with epilepsy due to an unknown cause have little increased risk. In the developing world, many deaths are due to untreated epilepsy leading to falls or status epilepticus.

Electroencephalography (EEG) is an electrophysiological monitoring method to record electrical activity of the brain. It is typically noninvasive, with the electrodes placed along the scalp, although invasive electrodes are sometimes used such as in electrocorticography. EEG measures voltage fluctuations resulting from ionic current within the neurons of the brain. EEG is most often used to diagnose epilepsy, which causes abnormalities in EEG readings.

EEG has a poor spatial resolution. Often for proper diagnosis and/or detection of epilepsy both high temporal resolution and spatial resolution are desired. Functional magnetic resonance imaging (MRI) and computed tomography (CT) can be used for detection of epileptic events. They provide good spatial resolution. However, they have poor temporal resolution. Moreover, they are expensive and not portable. Despite limited spatial resolution, EEG continues to be a valuable tool for research and diagnosis. It is one of the few mobile techniques available and offers millisecond-range temporal resolution which is not possible with CT, PET or MM.

Non-Invasive Epilepsy Treatment

The disclosed technology relates to a dual mode in the sense it detects and localizes the epileptic event in the order of milliseconds before the neural activity should lead to a seizure, and then it uses this information to focus ultrasound waves and suppress neuronal firings. The technology disclosed herein relates to detection of neural activity in a brain using acoustic waves, localization of the neural activity in the brain, and suppression of the neural activity in the brain in response to the detection and localization of the neural activity.

FIG. 1 is a flow diagram of a method 10 of detecting, localizing and suppressing neural activity in the brain according to an embodiment. The method 10 includes detecting neural activity in a brain using acoustic waves at block 12. The neural activity can correspond to a seizure. More detail regarding detecting neural activity will be provided with reference to FIG. 2. The method 10 includes localizing a source of the detected neural activity in the brain at block 14. The localization can be performed with resolution on the order of millimeters. The localization can involve applying machine learning techniques. More detail regarding localizing neural activity will be provided with reference to FIG. 3 and other figures. The method 10 also includes applying ultrasound energy to a source of the detected neural activity in the brain at block 16. This can suppress the neural activity. For example, this can suppress a seizure. More detail regarding applying ultrasound to the source of the neural activity in the brain will be provided with reference to FIG. 4.

Detection of Neural Activity with Acoustic Waves

Swelling of a single nerve fiber associated with an action potential can have a displacement of about 5 nanometers (nm) to 10 nm and a swelling pressure about half a Pascal (Pa). The frequency of the generated displacement centers around a few kilohertz (KHz). A seizure is expected to result from multiple action potential firings. Thus, a seizure should have a larger displacement from a larger source and generate more pressure than for a single action potential firing. An acoustic wave from a seizure can be detected using acoustic transducers, accelerometers, optical sound sensors, and/or any other suitable sensors. These sensors can provide a non-electrical method of detecting neural activity in the brain. Examples of acoustic transducers include piezoelectric transducers, capacitive micromachined ultrasonic transducers (CMUTs), electromagnetic acoustic transducers (EMATs), and the like.

Figure 6:
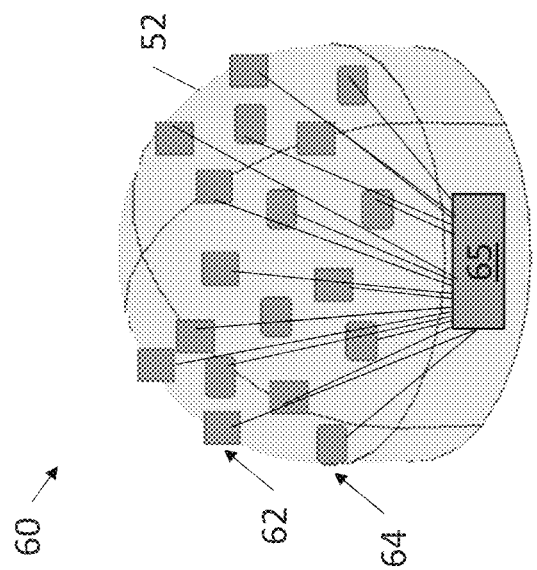
FIG. 6 illustrates a system for detecting and suppressing epileptic seizures according to an embodiment.

FIG. 2 is a flow diagram of a method 20 of detecting neural activity in the brain according to an embodiment. The method 20 can be implemented by block 12 of the method 10 of FIG. 1, for example. The method 20 includes sensing pressure waves associated with neural activity of a brain at block 22. Sensors positioned outside of a skull encasing the brain can detect the pressure waves. Accordingly, neural activity in the brain can be detected in a non-electrical and non-magnetic manner. The sensors can be positioned around the skull and arranged to take measurements at a plurality of locations. FIGS. 5 and 6 illustrate examples of such sensors. The sensors can be integrated with a helmet or cap, for example. In some instances, the sensors can be implanted between a skull and a scalp. The method 20 includes detecting a seizure based on outputs of the sensors at block 24. The outputs of the sensors can be processed. A seizure can be detected in response to sensed pressure waves indicating a seizure. For instance, the sensed pressure waves can match a pattern associated with a seizure. Alternatively or additionally, the sensed pressure waves can have a magnitude that satisfies a threshold pressure indicative of seizure. The outputs of the sensors can be processed and the seizure can be detected using a processor that is in communication with the sensors.

Localization of Neural Activity

The coupling into the skull can provide a unique texture into the acoustic waves. This can enable localizations of the source of a seizure to a few millimeters, even though the wavelength of the pressure wave is in the meter range. Moreover, each skull can have a different size, shape, etc. An acoustic wave can include compressional waves and/or shear waves. Compressional and/or shear waves can be utilized for localization. For instance, both compressional and shear waves can be used for localization. The feasibility of using both compressional and shear waves has been investigated via numerical simulations. At around 1 kHz, the compressional wave wavelength in the brain is on order of a meter. Hence, the detection is done in the near-field. However, the skull provides richness and unique texture to the detected data, making it possible to utilize machine learning techniques in localizing the event. For localization using compressional waves, a machine learning technique in conjunction with existing EEG localization techniques can be used. For localization using shear waves, since the wavelength in the brain at 1 kHz is much smaller, on the order of a few millimeters, detection is done in the far-field. Accordingly, beam-forming techniques can be used.

Localization of an epileptic event can be an inverse source problem where the locations of the events are inferred from recorded waveforms. Localization can include obtaining high resolution CT or MR images of a person. These images can then be processed to prepare the input to a computational model. The processing can include (a) segmentation and (b) registration and transformation. Segmentation can identify and separate each tissue type in the brain (such as skull, gray matter, white matter, skin, cerebral fluid, etc.). This can associate proper acoustic properties and boundary conditions in the model. Registration and transformation can properly mesh and map the patient-specific head geometry to the locations of the computational sources and receivers. This in-silico phantom can be fed into a forward/backward acoustic wave solver. The computational model can include finite elements, finite volumes, finite differences, boundary elements, spectral methods, the like, or any suitable combination thereof. The localization algorithm can be built upon this computational model. The localization algorithms can include compressional wave algorithms and/or shear wave algorithms.

With machine learning methods, a set of prior measurements at different sources with known locations can be used to estimate the location of an unknown source in any posterior measurement. The first step is called training and the second step is called estimation/localization. The training data are obtained using a person-specific computational model. The simulated waveforms at each receiver form a training set. Theses waveforms can be stacked together as columns of a matrix M. Let d(t) be an actual measurement. We can expand it as a linear combination of the bases (i.e., the training measurements). That is to write $$d(t) = \Sigma_{i=1}^{N} \theta_i d_i(y) + \in = \mathcal{M}\Theta + \in, \Theta \in \mathbb{R}^N,$$
$$\Theta = \langle \theta_1, \ldots, \theta_N \rangle^\dagger,$$

where di(t)'s are the training (computational) measurements and $\in$ is the error of the projection. We attempt to minimize the error in the localization step through, for example, least squares minimization, which can be represented by:

$$\min_{\Theta \in \mathbb{R}^N} \frac{1}{2} \sum_r \mu_r \|M_r \Theta - d_{r,s}\|^2_{l^2([0,T])}.$$

In this expression, $\mu_r$'s are weighting parameters. Mr and dr are the data matrix and the measured signal at the rth receiver. $\theta_i$'s are the projection coefficients, which give an estimate of the likelihood of finding the actual source at location i.

Possible variations include penalizing this optimization problem using a non-negativity constraint and/or sparse-promoting constraint (such as $l^1$ or $l^0$ penalty terms) to achieve a sparse and positive estimation of the projection coefficients.

An example compressional wave algorithm will now be discussed. The example compressional wave algorithm includes (a) machine learning for localization and (b) localization by comparing computational signals with measured signals. Since the computational model and training steps can both be performed once and/or prior to occurrence of an epileptic event, the localization step has a low computational burden/complexity and can be implemented on the order of a few milliseconds.

Since near field techniques can be used for the pressure waves, a learning method can be used for localization. An example process involves running a person-specific forward computational model for as many sources as adequate, where the sources are separated by the desired resolution (e.g., a millimeter) and cover a volume of interest.

Localization by comparing the computational signals with the measured signals can be performed, for example, using one or more of the following methods: custom projection-based learning, deep and convolutional neural network models, or other machine learning techniques including classifiers (such as Support Vector Machine (SVM), softmax regression, generalized linear models, etc.) and regression techniques.

In custom projection-based learning methods, the computational data are stacked together to form several data spaces for each receiver. The algorithm can attempt to find a projection of the measured signal onto the data spaces. The bases of the space with the maximum shadow (projection) of the measured signal can be identified as the source.

In deep and convolutional neural network model methods, a deep or convolutional neural network is trained based on the computational sources and simulated waveforms. The measured signal in presence of an epileptic event can then be fed into the already trained neural network model to predict the location of the source.

Example shear wave algorithms will now be discussed. Since the wavelength for the shear waves is on an order of a millimeter, one or more of a variety of source imaging/localization techniques can be used. Examples of such techniques include (1) tomographic reconstruction, (2) adjoint-state localization, (3) beam-forming (delay-sum and/or its variants), (4) sparse array imaging, (5) time-reversal techniques (including DORT and MUSIC), and (6) correlation-based methods.

FIG. 3 is a flow diagram of a method 30 of localizing a source of neural activity in the brain according to an embodiment. Any suitable part of the method 30 can be implemented at block 14 of the method 10 of FIG. 1. Any suitable part of the method 30 can be performed using any suitable processor. Localization can be an inverse problem. Parameter functions can be non-linearly mapped to data. Accordingly, localizing can involve estimating the non-linear mapping. Machine learning techniques can be applied. The brain and skull can be treated as a black box and machine learning can be implemented experimentally.

The method 30 includes modeling a brain and skull at block 32. The shape and size of a skull can be determined, for example, using a CT scan. For various event locations, pressure waves at points on the skull can be calculated. The model can be developed, for example, by detecting pressure waves associated with neural events using sensors and comparing the measurements by the model to where the source of the event is determined to be using another method, such as a CT scan. Then the model can be refined. Pressure waves associated with neural activity in the brain, such as a seizure, can be detected at block 34. This operation can correspond to block 12 of the method 10 of FIG. 1 in certain instances. The data associated with the detected pressure waves can be compared with the model at block 36. Then the source of the neural activity can be determined at block 38. The source can be determined resolution on the order of millimeters.

Suppression of Neural Activity with Ultrasound

Once the seizure is localized with millimeter resolution, ultrasonic transducers at relatively high frequencies (e.g., in range from 0.5 MHz to 5 MHz) can be used suppress the action potential firings. This can blunt the seizure. Ultrasound energy has been shown to have reversible inhibitory effects, through macroscopic temperature elevation in the brain. The relatively high frequency ultrasonic transducers can be integrated into the same helmet as the acoustic transducers or other sensors for detecting the seizure. Any suitable technology can be used for ultrasonic transducers for suppressing a seizure. For instance, piezoelectric ultrasonic transducers and/or capacitive micromachined ultrasonic transducers (CMUTs) can be used for suppressing neural activity in the brain.

Ultrasound energy can be delivered to the brain using techniques for transcranial ultrasound delivery in certain instances. An array of ultrasonic wedge transducers arranged to efficiently deliver focused ultrasound energy into the brain with relatively minimal heating of the skull can be used. The ultrasonic wedge transducers can have a treatment envelope of an entire brain or substantially the entire brain. The ultrasound wedge transducers can generate Lamb waves that then mode convert into longitudinal waves in the brain. Alternatively or additionally, a 2-dimensional array of ultrasonic transducers can generate Lamb waves by applying signals with the appropriate phases and at a proper frequency to favor the generation of a certain mode of Lamb waves for transcranial ultrasound delivery. Any other suitable technique of delivering ultrasound can be implemented for applying ultrasound energy to a source of neural activity in the brain. Such techniques can include, for example, normal incidence techniques.

Suppression of neural activity using ultrasound energy can be performed in response to detecting neural activity and localizing a location of the neural activity. Ultrasound energy can be applied to the location of the neural activity within a millisecond time frame of swelling of nerve fibers in the brain. Moreover, the ultrasound energy can be applied to a location that is determined with resolution on the order of a millimeter. As such, ultrasound suppression of neural activity disclosed herein can be a dynamic treatment applied in a specific location in response to an event.

FIG. 4 is a flow diagram of a method 40 of suppressing neural activity in the brain according to an embodiment. The method 40 can be implemented by block 16 of the method 10 of FIG. 1, for example. The method 40 includes receiving information identifying a location of neural activity in the brain at block 42. This information can be received in response to detection and/or localization of the neural activity. Ultrasound energy can be applied to the location in the brain at block 44. The ultrasound energy can have a frequency in a range from 0.5 MHz to 5 MHz, for example. In cases where a skull is relatively thin, the ultrasound energy can be in a higher part of the range (e.g., 1 MHz to 5 MHz). This can achieve advantages in focusing and/or suppression. As an example, a child can have a relatively thinner skull than an adult. In some instances, the ultrasound energy can have a frequency in a range from 0.5 MHz to MHz. The ultrasound energy can be applied using transcranial ultrasound delivery techniques that result in a relatively small amount of heating of the skull.

Example Systems for Detection, Localization, and Suppression of Seizures

The forward problem has been modeled, showing through numerical analysis that pressure waves with varying characteristics are present at different locations over a skull. This difference in the pressure waves at various locations confirms that it is possible to localize an event even with such a large wavelength. Various types of sensors can be used to detect seizures. A swim cap-like helmet can be used in which a number of acoustic transducers and/or other suitable sensors, such as accelerometers, are included for detection and suppression of epileptic seizures. Example systems that can be used to perform any suitable features of detection, localization, and/or detection of seizures disclosed herein will now be discussed. The detection, localization, and suppression of neural activity can be performed in milliseconds so that adverse effects of neural activity in the brain are mitigated and/or not realized.

FIG. 5 illustrates an example system 50 for detecting and suppressing epileptic seizures according to an embodiment. As illustrated, the system 50 is positioned relative to a human head. The system 50 can be used to perform any suitable operations of any of the method disclosed herein. The system 50 includes a helmet 52 and integrated acoustic transducer arrays 54. The helmet 52 can be any suitable helmet. The helmet 52 can be soft or hard. In certain instances, the helmet 52 can be similar to an EEG cap. A headset with a plurality of sensors and/or acoustic transducers can alternatively be implemented. The acoustic transducers 54 can be used to detect an epileptic event, localize a location 56 of the epileptic event, and to apply focused ultrasound to the location 56 of the epileptic event. A schematic of an example 2-dimensional array of acoustic transducers 54 is also shown. A plurality of these arrays of acoustic transducers 54 can be integrated with the helmet 52 to provide a plurality of locations from which to generate data associated with pressure waves and/or from which to apply ultrasound to the location 56. The acoustic transducers 54 are in communication with a processor. The processor can process signals from the acoustic transducers 54. Accordingly, the processor can be used to detect and/or localize a seizure. The processor can provide inputs to cause the acoustic transducers 54 to apply focused ultrasound. The processor can be integrated with the helmet 52 and/or external to the helmet 52. The processor can be in communication with the acoustic transducers 54 by wired connections and/or wirelessly.

FIG. 6 illustrates an example system 60 for detecting and suppressing epileptic seizures according to an embodiment. The system 60 can be used to perform any suitable operations of any of the method disclosed herein. The system 60 includes a helmet 52, integrated sensors 62, integrated ultrasonic transducers 64, and a processor 65. In the system 60, the sensors 62 used to detect and/or localize an epileptic event are separate from the ultrasonic transducers 64 arranged to apply focused ultrasound to suppress the epileptic event. The sensors 62 and ultrasonic transducers 64 can operate at different frequencies. Accordingly, a separate implementation can allow both the sensors 62 and the ultrasonic transducers 64 to be configured for operating at respective desired frequencies.

The sensors 62 can provide data associated with pressure waves at a plurality of locations on a skull. The sensors 62 can include acoustic transducers, accelerometers, other suitable pressure sensors, or any suitable combination thereof. As one example, the sensors 62 can include acoustic transducers with a resonant frequency in the kHz range. The ultrasonic transducers 64 can apply focused ultrasound from a plurality of locations around the skull. The ultrasonic transducers 64 can be configured for transcranial ultrasound delivery. For instance, the ultrasonic transducers 64 can include an array of ultrasonic wedge transducers. The ultrasonic transducers 64 can apply focused ultrasound energy having a frequency on the order of 100s of kHz. The sensors 62 and the ultrasonic transducers 64 are in communication with a processor 65. For example, the sensors 62 and the ultrasonic transducers 64 can be electrically connected to the processor 65 via wired connections as illustrated.

The processor 65 can perform any suitable processing on the output of the sensors 62 to detect and/or localize the epileptic event. For instance, the processor 65 can be used to implement any suitable operations of detecting and/or localizing neural activity disclosed herein. The processor 65 can include any suitable circuitry arranged to perform such processing. The processor 65 can control the ultrasonic transducers 64 to apply focused ultrasound to a location of an epileptic event in response to detecting and localizing the epileptic event. The processor 65 and the ultrasonic transducers 64 can be used to implement any suitable operations related to applying focused ultrasound disclosed herein. Although the processor 65 is integrated with the helmet 52 in FIG. 6, the processor 65 can be partly or fully separate from the helmet 52 in some instances.

Although the systems of FIGS. 5 and 6 include helmets, any suitable principles and advantages disclosed herein can be implemented without a helmet. For instance, sensors 62 and/or acoustic transducers 54 and/or ultrasonic transducers 64 can be implanted between the scalp and the skull and perform similar or the same functionalities.

Modeling and Simulation

The skull and brain can be modeled for a specific person. For instance, skulls for young people can be relatively thinner than skulls for older people. Thinner skulls can be amenable to relatively higher frequency ultrasound than thicker skulls. Accordingly, the frequency of ultrasound used for suppressing neural activity can be adjusted for a particular skull. Moreover, one or more other parameters can alternatively or additionally be adjusted as suitable based on characteristics of a particular skull.

The model can treat the skull as a circularly symmetric model, a 3-dimensional spherical model, or a full 3-dimension model of a particular human head with anatomical features. A circularly symmetric configuration was first investigated due to lower computation burden than a 3-dimensional model. How much texture/feature the presence of the skull can add to measurements at different points on the skull was investigated. The order of displacements that can be detected and what kind of sensitivity and bandwidth for detection of a seizure were studied. The feasibility of detecting shear waves as well as compressional waves has also investigated. A 3-dimensional model with a hemispherical skull was constructed. The models were utilized for developing localization algorithms.

Figure 7B:
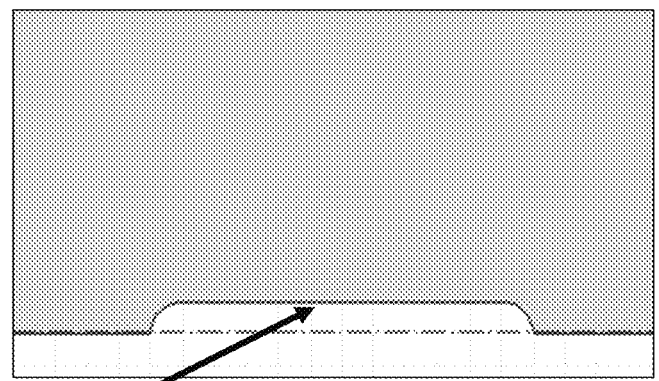
FIG. 7B illustrates a representation of a pressure wave with particular input normal surface velocity, width, and height at a location of the skull of FIG. 7B.
Figure 7A:
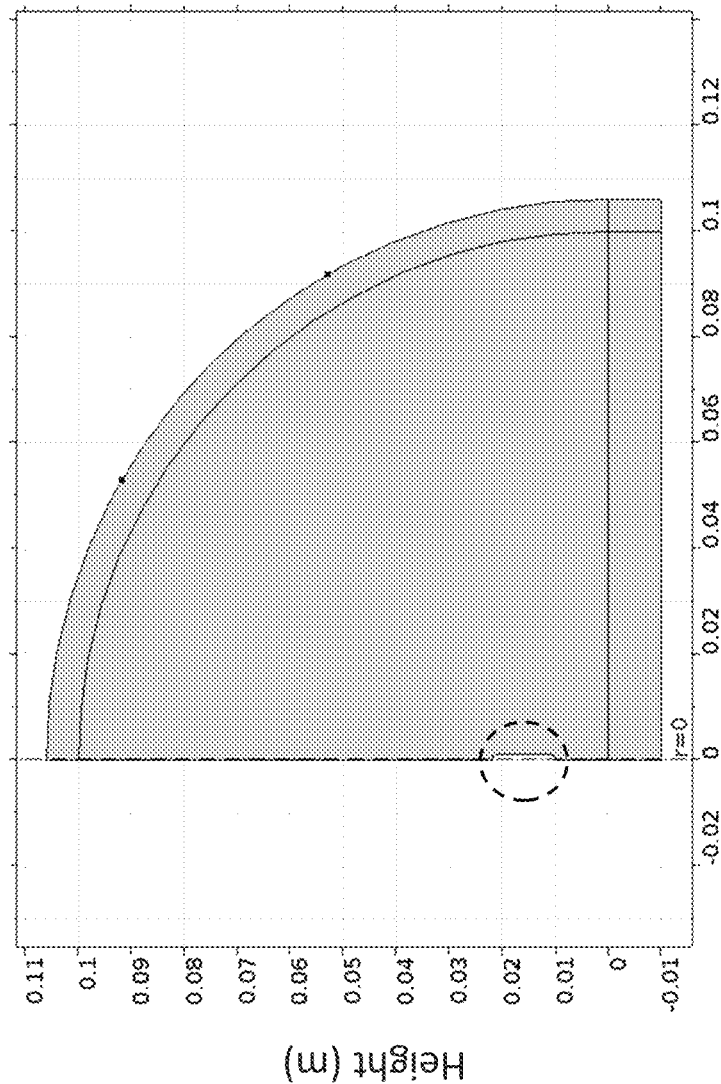
FIG. 7A is a representation of a portion of a skull.
Figure 7C:
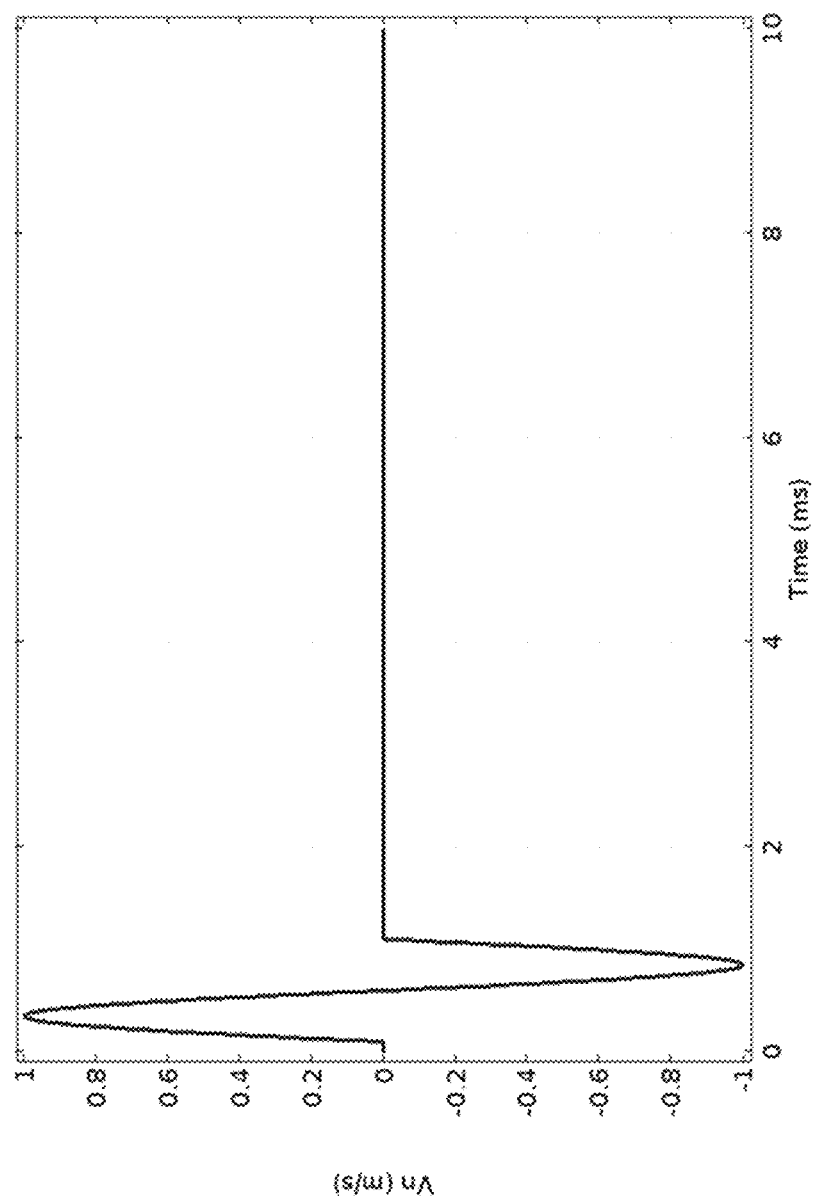
FIG. 7C shows an input velocity profile used to simulate pressure generated along a central axis of the skull of FIG. 7A.

FIG. 7A is a representation of a portion of a circular skull with a radius of 10 cm. FIG. 7B illustrates a representation of an acoustic wave with an input normal surface velocity of 1 m/s with a width of 2 mm and a height of 10 mm. FIG. 7C shows an input velocity profile used to simulate pressure generated along a central axis of the skull. The results on the y-axis in FIG. 7C are normalized. The simulation is linear. Thus, the results can be scaled to a desired/actual velocity to estimate an output. The resulting pressure wave at a plurality of points on the skull can then be measured. In the simulations, the skull bone was modeled an elastic solid that supports shear waves.

Figure 8B:
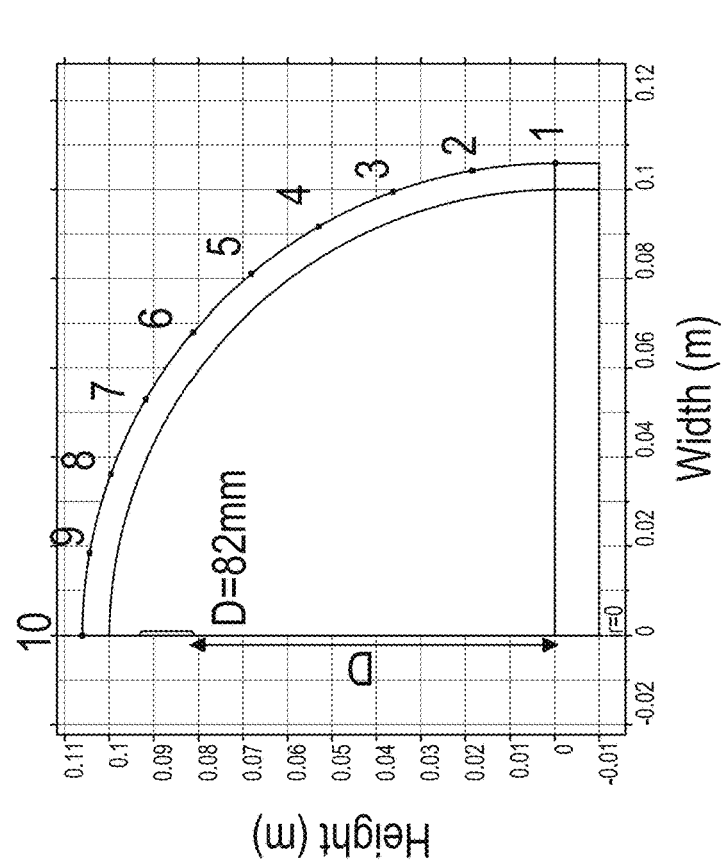
FIG. 8B illustrates 10 points on the skull of FIG. 7A where a pressure wave can be measured for a second location of a source of neural activity.
Figure 8A:
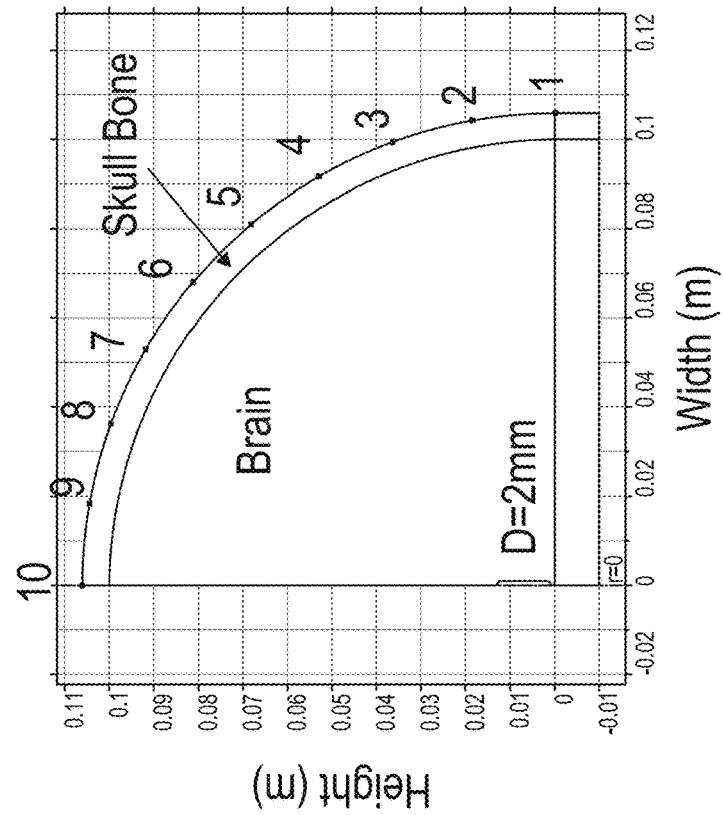
FIG. 8A illustrates 10 points on the skull of FIG. 7A where a pressure wave can be measured for a first location of a source of neural activity.

FIGS. 8A and 8B illustrate 10 points on the skull where the pressure wave can be measured for different locations of a source of neural activity. While 10 points are used in example simulations, any suitable number of measurement points can be used. The source of neural activity simulates nerve fibers swelling. The measurement points can be evenly distributed as illustrated. The source of neural activity is located at different points along the central axis in FIGS. 8A and 8B. In FIG. 8A, the source is located at a first location that is 2 mm from the center point along with central axis. In FIG. 8B, the source is located at a second location that is 82 mm from the center point along the central axis. The skull around the brain tissue impacts the pressure wave measurements at the measurement points on the skull.

Figure 9A:
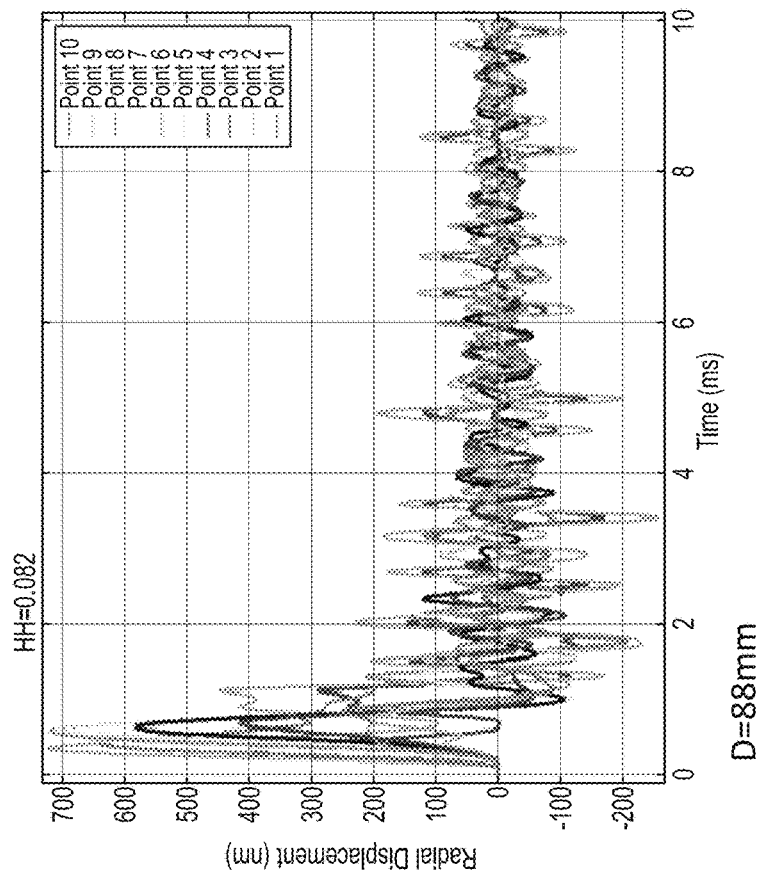
FIG. 9A is a graph of radial displacement normal to the surface of a skull based on compressional waves at 10 points for the first location of the source of neural activity shown in FIG. 8A.
Figure 9B:
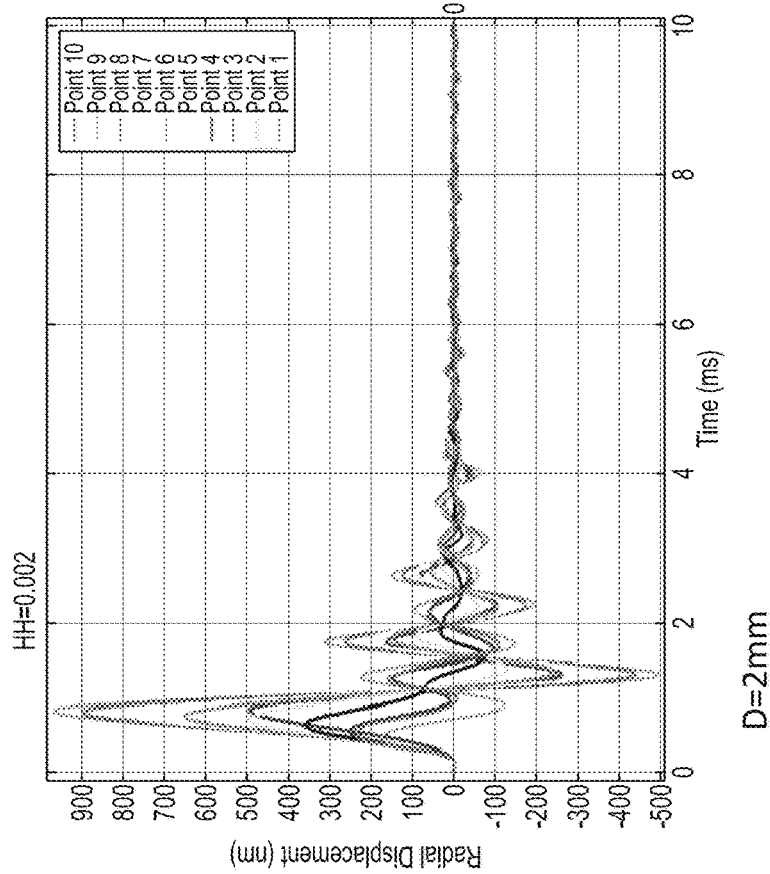
FIG. 9B is a graph of radial displacement normal to the surface of a skull based on compressional waves at 10 points for the second location of the source of neural activity shown in FIG. 8B.

FIGS. 9A and 9B are graphs of radial displacement normal to the surface of the skull based on compressional waves. Graphs for the 10 points on the skull from FIGS. 8A and 8B are shown. These simulations assume that the brain issue does not support shear waves. FIG. 9A illustrates pressure sensor signals for the source located at 2 mm from the center point along the center axis as shown in FIG. 8A. FIG. 9B illustrates pressure sensor signals for the source located at 82 mm from the center point along the center axis as shown in FIG. 8B. The location of the source can be identified by training a model to identify where the location of the source is based on corresponding sensor outputs at the measurement points on the skull.

Figure 10A:
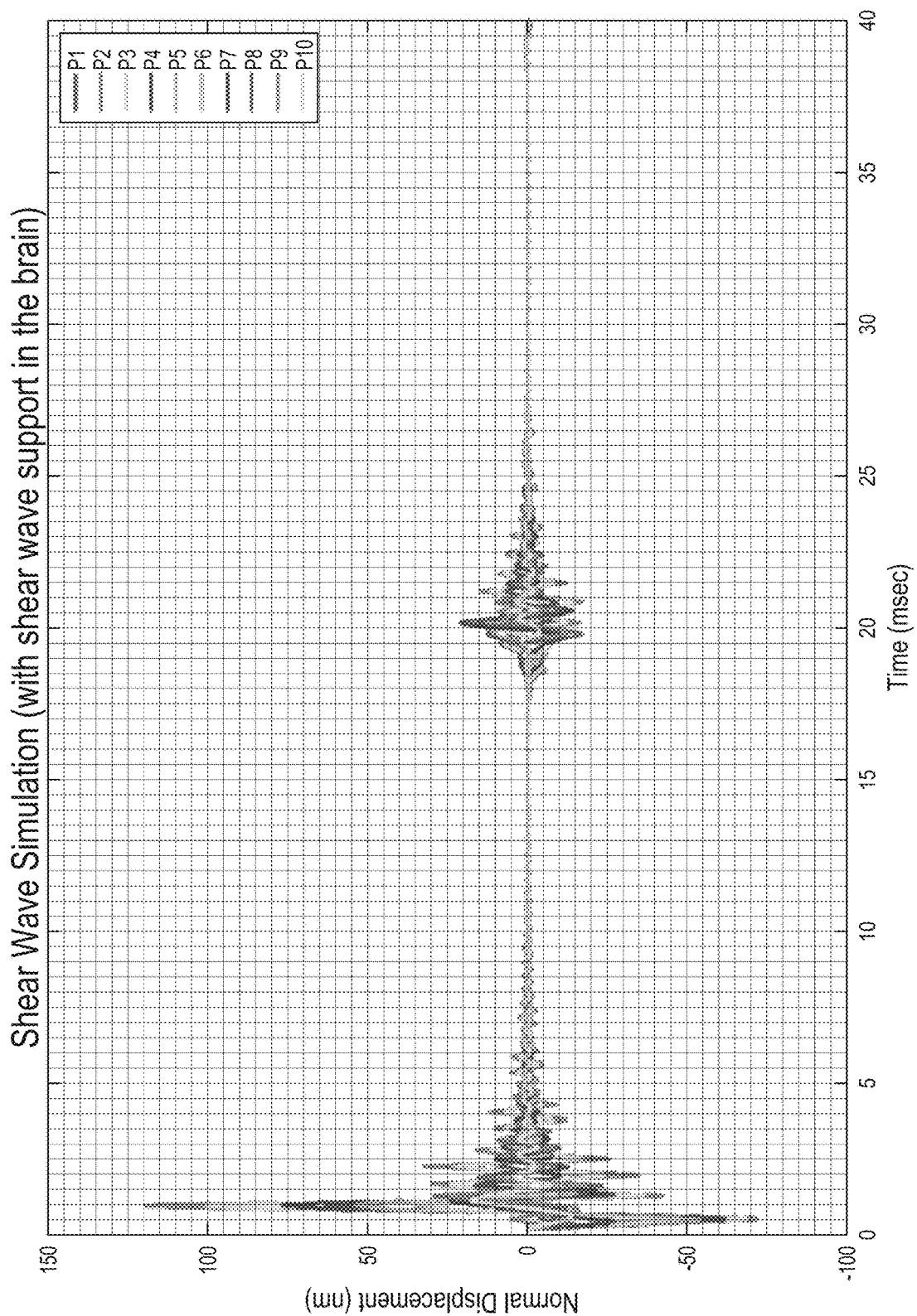
FIG. 10A is a graph of radial displacement normal to a surface of a skull based on shear wave simulation at 10 points for the first location of the source of neural activity shown in FIG. 8A.
Figure 10B:
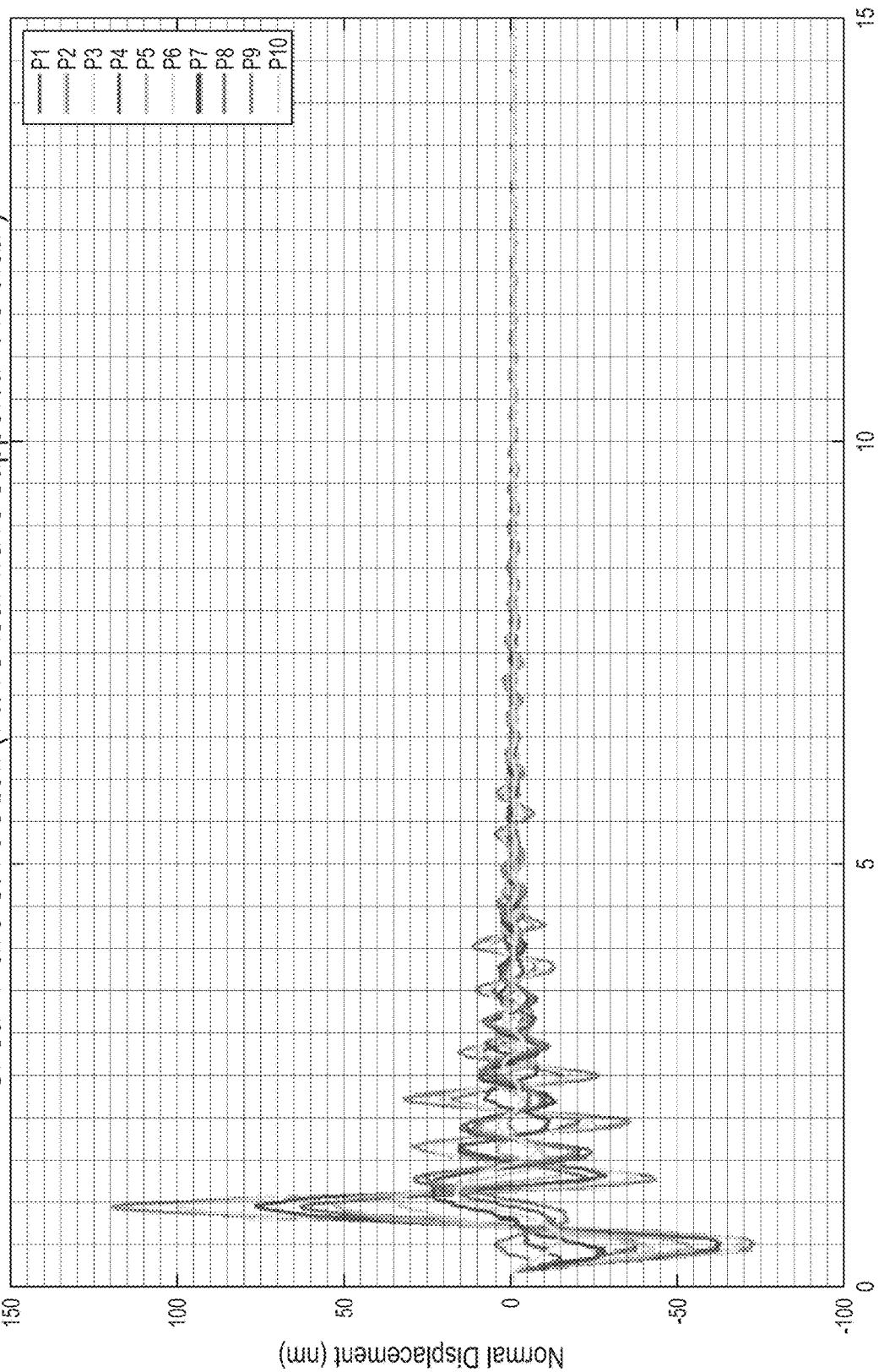
FIG. 10B is a zoomed in view of one portion of the graph of FIG. 10A.
Figure 10C:
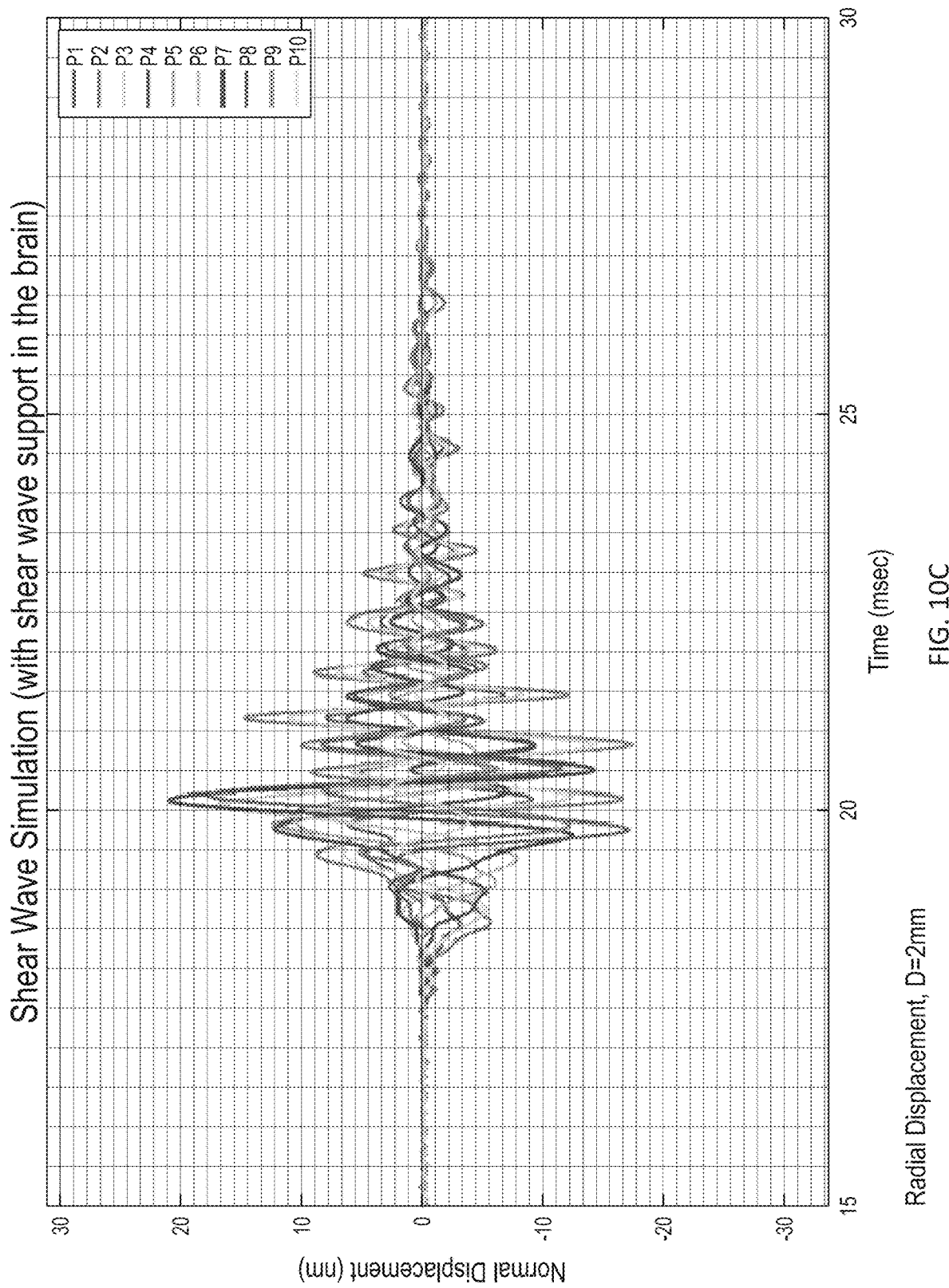
FIG. 10C is a zoomed in view of another portion of the graph of FIG. 10A.

FIG. 10A is a graph of radial displacement normal to the surface of the skull based on shear wave simulation. Using shear waves is a different localization technique than using compressional waves. FIGS. 10B and 10C are graphs that zoom in on different portions of the graph of FIG. 10A. These graphs correspond to a source of neural activity located at 2 mm from the center point along the center axis as shown in FIG. 8A and each curve is for a different one of the 10 measurements points shown in FIG. 8A. At time equals about 20 milliseconds, a new wave packet is generated. A model can be constructed based on back propagation beamforming. The location of the source can be identified by training a model to identify where the location of the source is based on corresponding sensor outputs at the measurement points on the skull.

Figure 11A:
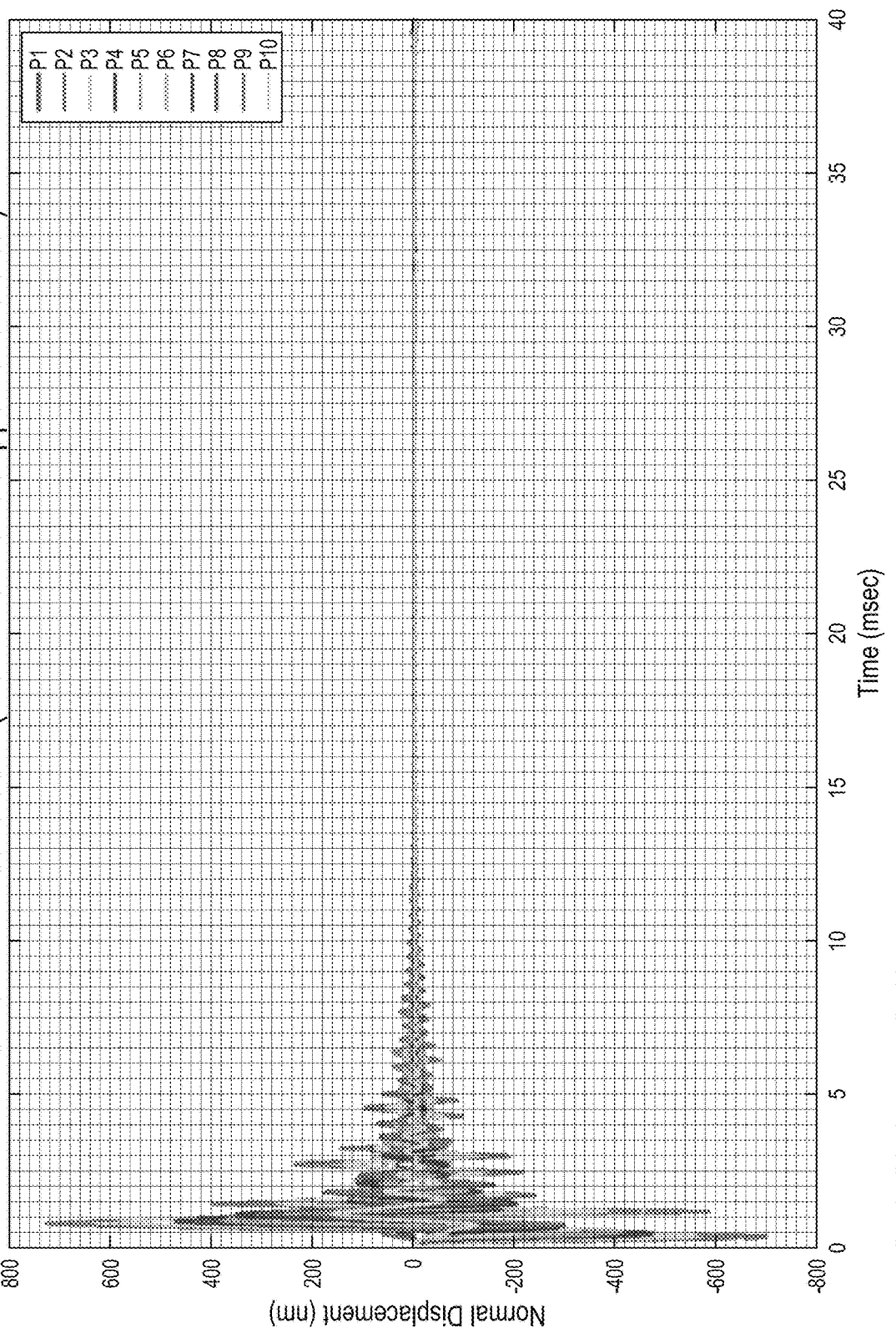
FIG. 11A is a graph of radial displacement normal to a surface of a skull based on shear wave simulation at 10 points for the second location of the source of neural activity shown in FIG. 8B.
Figure 11B:
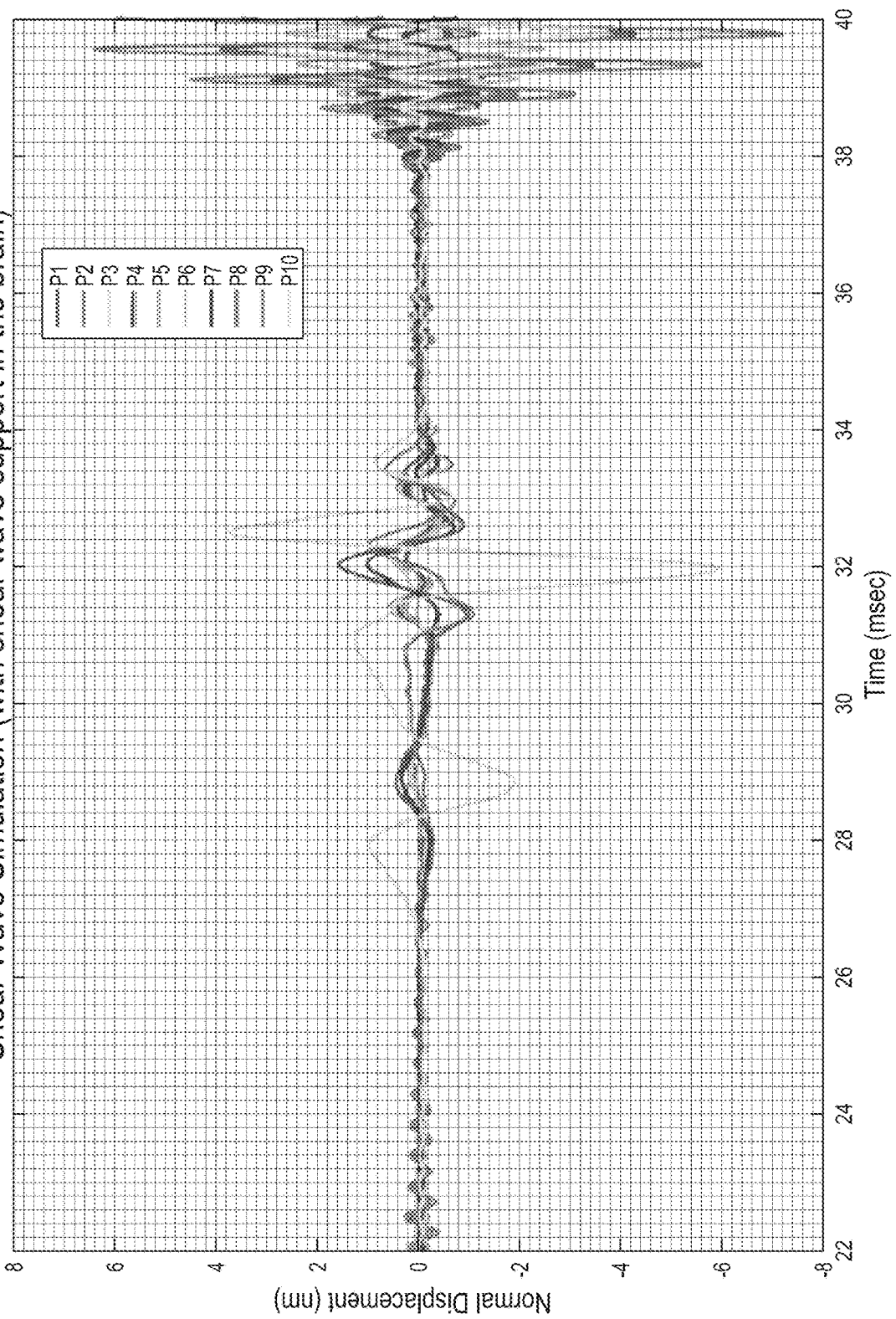
FIG. 11B is a zoomed in view of one portion of the graph of FIG. 11A.
Figure 11C:
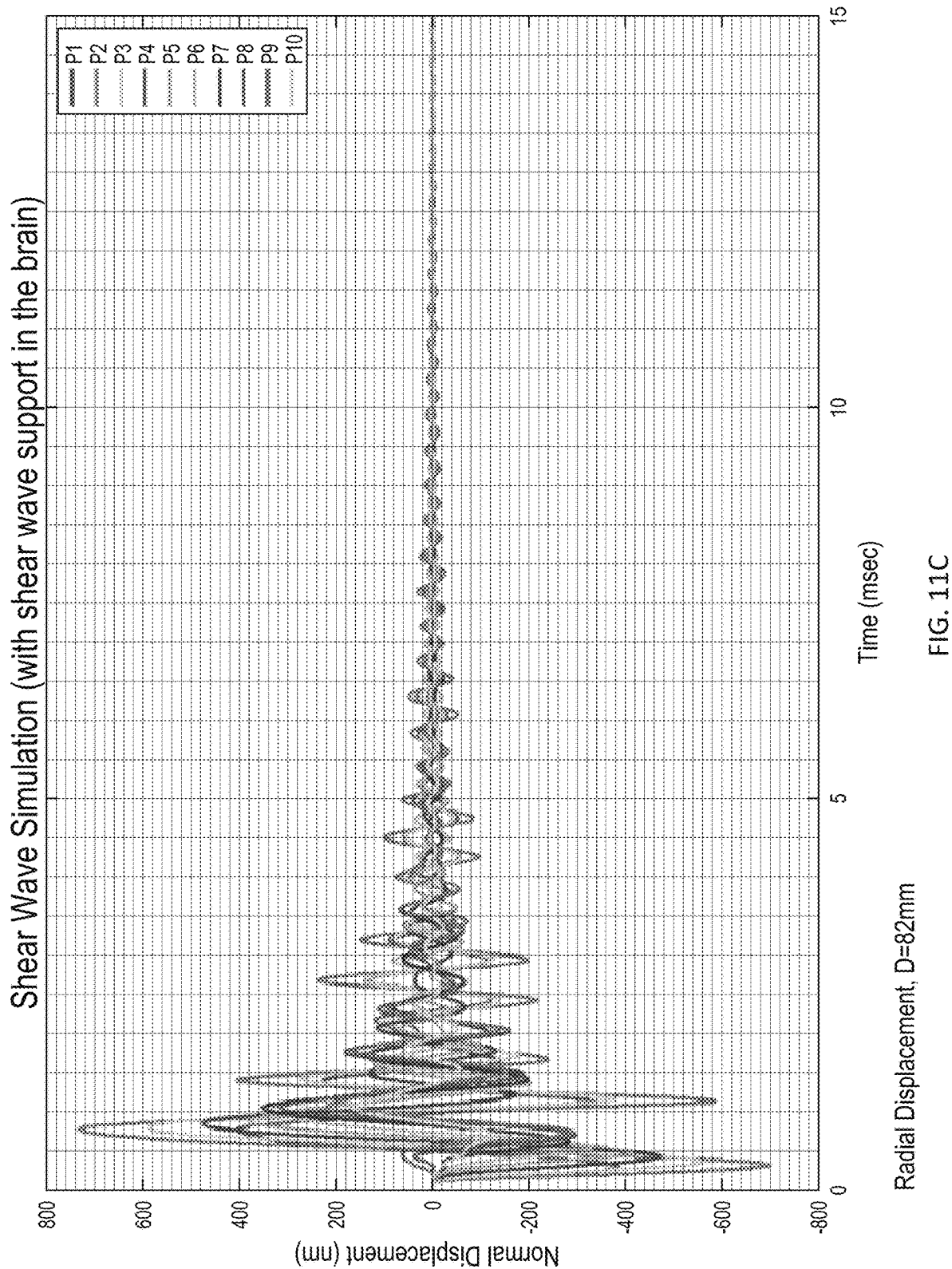
FIG. 11C is a zoomed in view of another portion of the graph of FIG. 11A.

FIG. 11A is a graph of radial displacement normal to the surface of the skull based on shear wave simulation where the source is at a different location than for FIG. 10A. FIGS. 11B and 11C are graphs that zoom in on different portions of the graph of FIG. 11A. These graphs correspond to a source of neural activity located at 82 mm from the center point along the center axis as shown in FIG. 8B and each curve is for a different one of the 10 measurements points shown in FIG. 8B. A model can be constructed based on data corresponding to sources at a variety of locations within the brain.

Figure 12B:
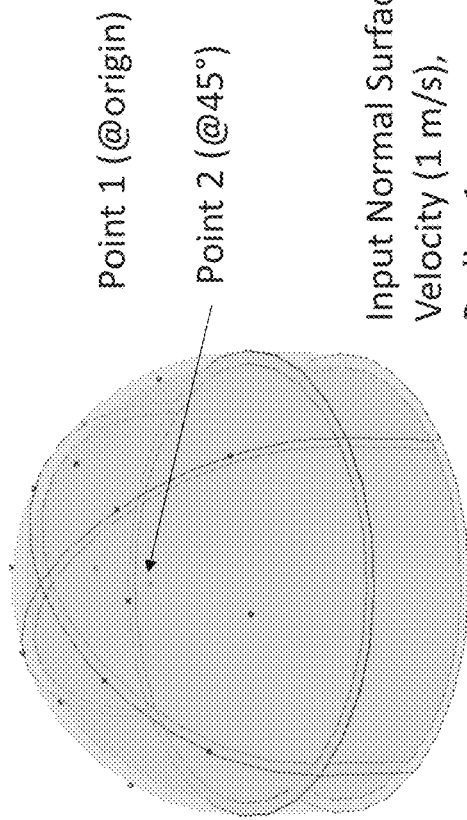
FIG. 12B shows two source points associated with the hemispherical skull of FIG. 12A.
Figure 12A:
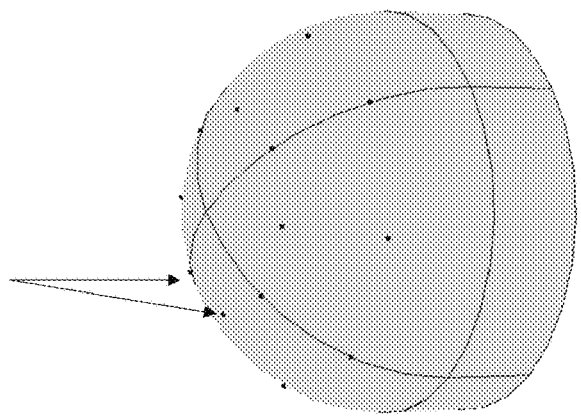
FIG. 12A is an illustration corresponding to a 3-dimensional model of a hemispherical skull.

FIG. 12A is an illustration corresponding to a 3-dimensional model of a hemispherical skull. There are 16 distributed measurement points on the illustrated hemispherical skull. FIG. 12B shows two source points associated with the hemispherical skull, in which a first point is at the origin and a second point is at 45°. An input normal surface velocity of 1 m/s with a radius of 1 mm was simulated at each source point.

Figure 13A:
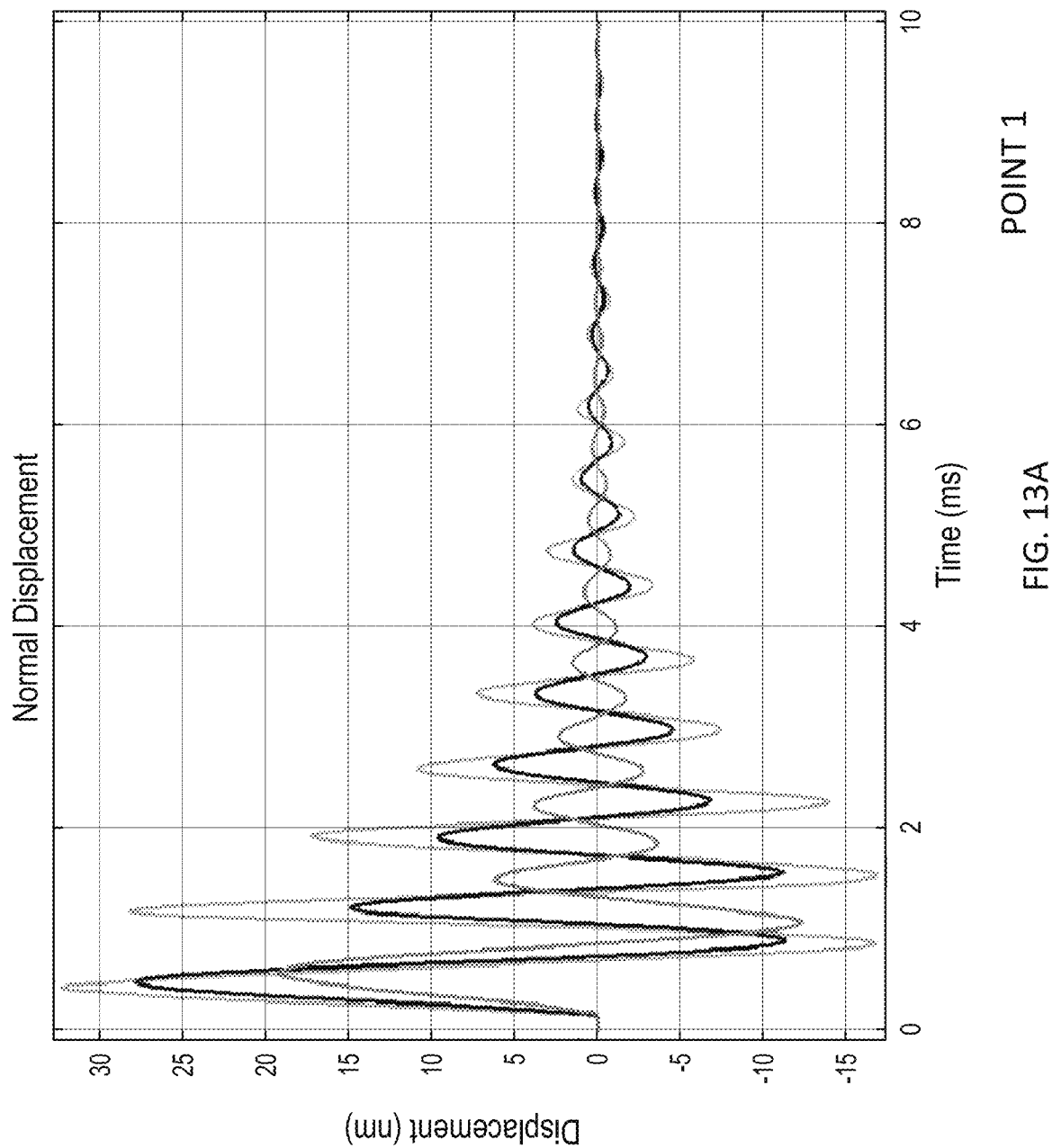
FIG. 13A illustrates normal displacements over time for various measurement points associated with a first source point of the two source points shown in FIG. 12B.
Figure 13B:
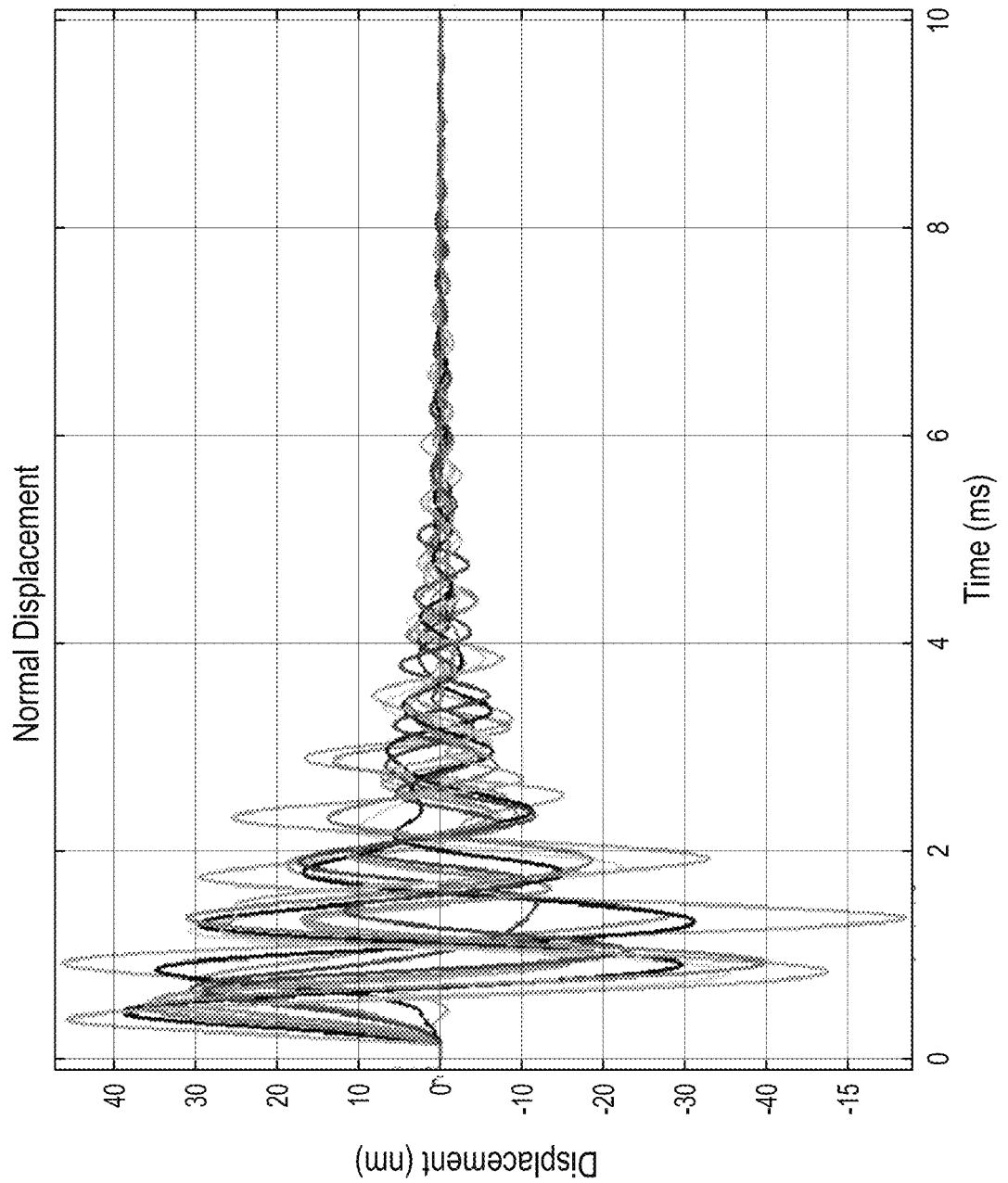
FIG. 13B illustrates normal displacements over time for various measurement points associated with a second source point of the two source points shown in FIG. 12B.

FIG. 13A illustrates normal displacements over time for various measurement points associated with the first source point of FIG. 12B. FIG. 13B illustrates normal displacements over time for various measurement points associated with the second source point of FIG. 12B. The location of the source can be identified by training a model to identify where the location of the source is based on corresponding sensor outputs at the measurement points on the skull.

Accordingly, compressional waves and/or shear waves can be used for detection and localization of an epileptic event. Displacement data on the outer surface of the skull is normalized in the simulations herein. The model is linear and thus can be scaled based on the order of displacement of an epileptic firing.

The simulations herein illustrate that the skull and its complicated nature provides enough features to distinguish signals at different locations and thus it provides the capability of localizing an epileptic event in the near-field.

The resolution of localization can be bounded by the resolution of the training points used to develop a model. In other words, the separation between sources of neural activity used in a training step of a localization algorithm can determine the resolution of reconstruction for the localization algorithm.

Figure 14A:
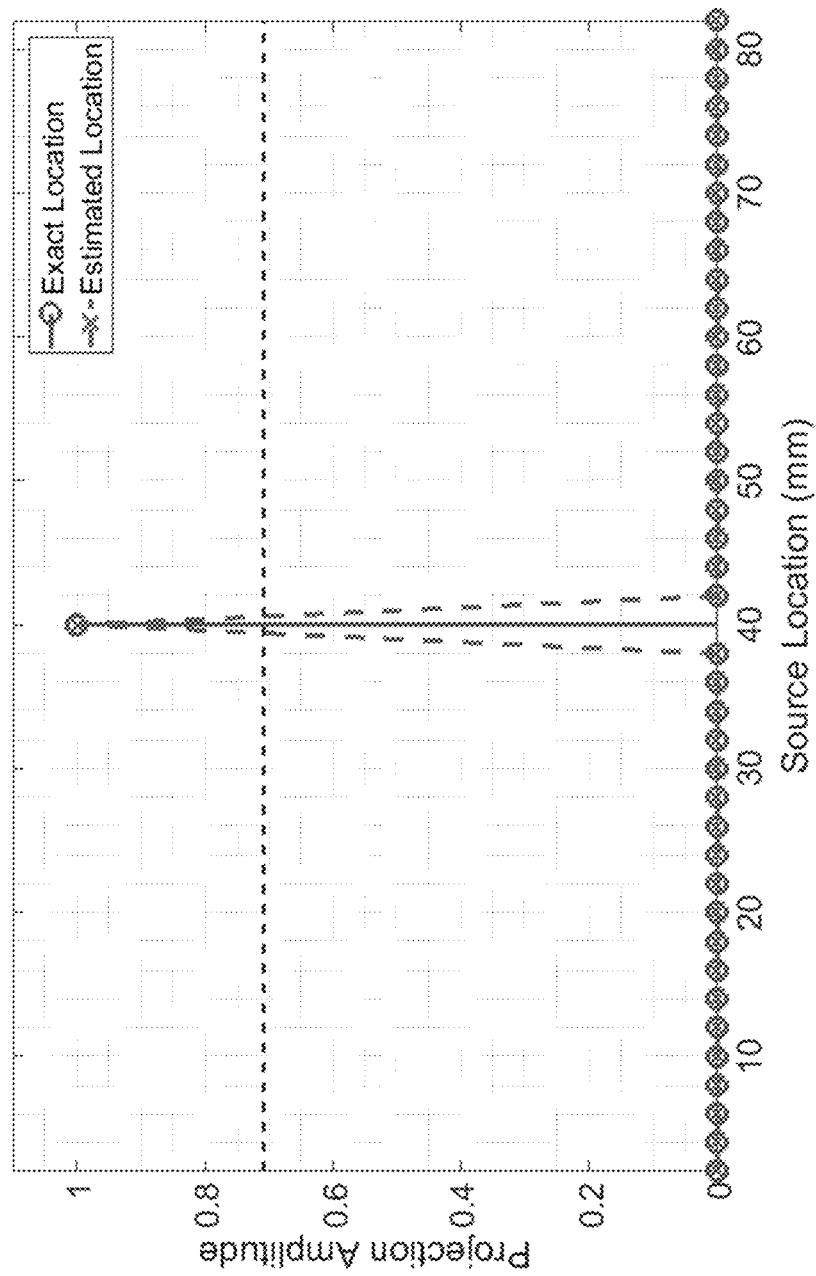
FIG. 14A is a graph for a simulation of localizing a source of neural activity at a location used in training.
Figure 14B:
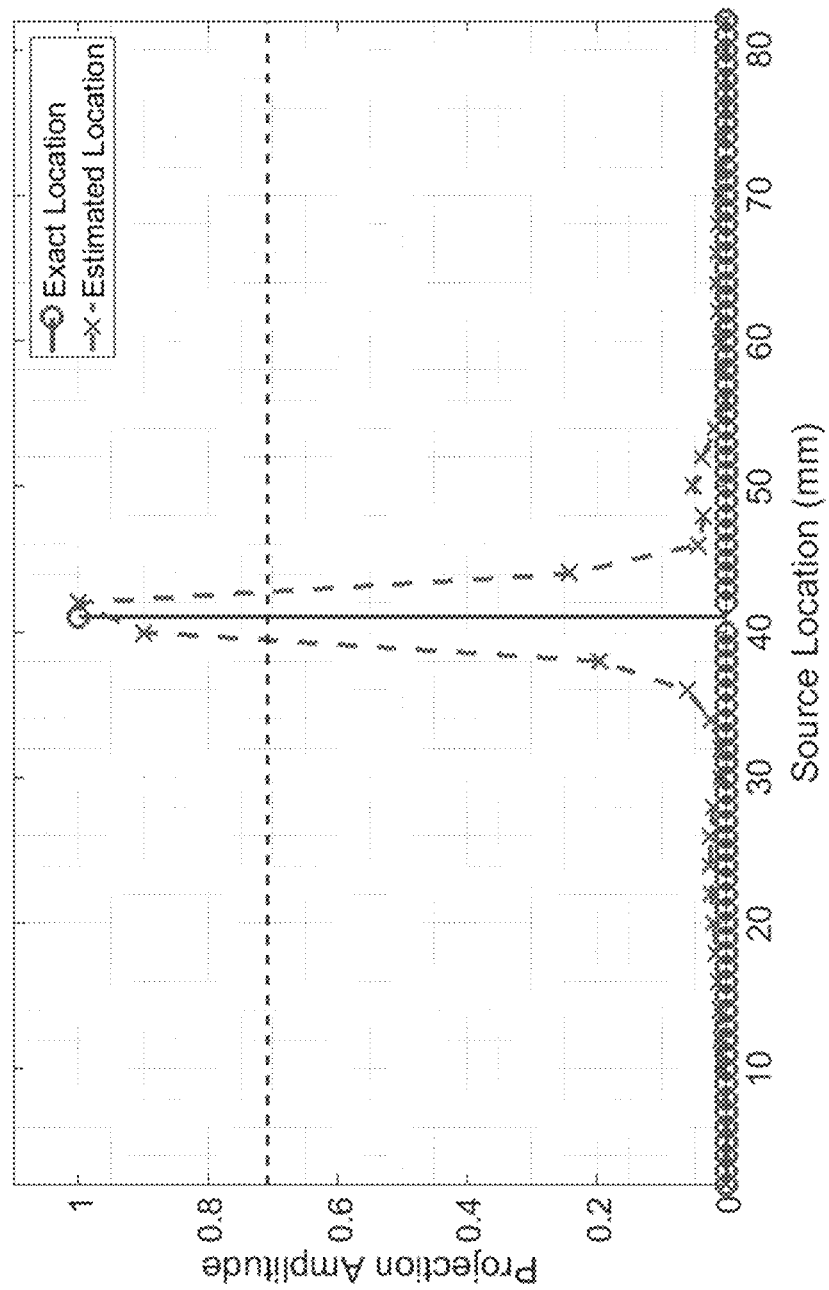
FIG. 14B is a graph for a simulation of localizing a source of neural activity located at a point in between two locations of neural activity of the training set.

FIGS. 14A and 14B illustrate results from localization simulations. In the simulations corresponding to FIGS. 14A and 14B, the model is assumed to be noise free. In FIGS. 14A and 14B, a horizontal dashed line shows the 3 decibel (dB) point, which was used to estimate resolution. The curve with circle data points shows the location of an unknown source. The dashed curve with x data points shows what a localization algorithm estimates as the likelihood of finding the unknown source are various locations at points used to train a model.

The best case scenario for localization can be when the algorithm tries to localize a source at a location that has been used in training the model. FIG. 14A corresponds to localizing a source at a location used in training. In the simulations corresponding to FIGS. 14A and 14B, a model was trained by sources evenly distributed 2 mm apart. FIG. 14A indicates a resolution of about 1.16 mm. This can bound resolution for localizing with the training set for this simulation. For a better resolution, the model can be trained with a smaller source separation.

FIG. 14B corresponds to simulation results for localizing a source located at a point in between two locations of the training set. The localization algorithm can interpolate the location of the source in between the two points in the training set. FIG. 14B corresponds to a lower resolution than FIG. 14A. FIG. 14B indicates a resolution of about 3.16 mm.

Applications and Conclusion

The disclosed innovations are not specific to a particular application or technology for implementation. Other applications include the use of the transducers to detect the character of normal brain mechanical impulses in daily life conditions. The premise is that different emotions or states of mind would result in different characteristics of the mechanical brain waves. One would then be able to localize the origin of certain feelings like anger, to certain locations in the brain, then suppress such feelings before they result in action. This can then be extended to enhancing good feelings in the same fashion.

Because every person's skull can be different, a CT scan can be done on each individual in order to tailor make an algorithm for detection and suppression of neural activity. Other imaging modalities are envisaged to provide the skull shape and outline for algorithm development.

Some of the embodiments described above have provided examples in connection with epileptic seizures in the brain. However, the principles and advantages of the embodiments can be used for any other suitable devices, systems, apparatuses, and/or methods that could benefit from such principles and advantages.

The various features and processes described herein may be implemented independently of one another, or may be combined in various ways. All possible combinations and sub combinations are intended to fall within the scope of this disclosure. In addition, certain methods or process blocks may be omitted in some implementations. The methods and processes disclosed herein are also not limited to any particular sequence, and the blocks or states relating thereto can be performed in any other sequences that are appropriate. For example, described blocks or states may be performed in an order other than that specifically disclosed, or multiple blocks or states may be combined in a single block or state. The example blocks or states may be performed in serial, in parallel, or in some other manner as appropriate. Blocks or states may be added to or removed from the disclosed example embodiments as suitable. The example systems and components described herein may be configured differently than described. For example, elements may be added to, removed from, or rearranged compared to the disclosed example embodiments.

While certain embodiments have been described, these embodiments have been presented by way of example only, and are not intended to limit the scope of the disclosure. Indeed, the novel devices, systems, apparatus, methods, and systems described herein may be embodied in a variety of other forms; furthermore, various omissions, substitutions and changes in the form of the methods and systems described herein may be made without departing from the spirit of the disclosure. For example, while blocks are presented in a given arrangement, alternative embodiments may perform similar functionalities with different components and/or circuit topologies, and some blocks may be deleted, moved, added, subdivided, combined, and/or modified. Each of these blocks may be implemented in a variety of different ways. Any suitable combination of the elements and acts of the various embodiments described above can be combined to provide further embodiments.

What is claimed is:

1. A system for detecting seizures, the system comprising:
   sensors configured to detect, from outside of a skull encasing a brain, acoustic waves associated with neural activity in the brain; and a processor in communication with the sensors, the processor configured to process output signals from the sensors, to detect a seizure based on the output signals from the sensors, and to localize a source of the seizure with millimeter scale resolution.

2. The system of claim 1, wherein the acoustic waves comprise compressional waves having a wavelength on the order of a meter.

3. The system of claim 1, wherein the processor is configured to localize the source of the seizure with machine learning techniques.

4. The system of claim 1, further comprising ultrasonic transducers in communication with the processor, the processor configured to control the ultrasonic transducers to apply ultrasound to the source of the seizure in response to detecting the seizure.

5. The system of claim 4, wherein the processor is configured to control the ultrasonic transducers to apply the ultrasound within a millisecond time range from receiving the output signals from the sensors.

6. The system of claim 1, wherein the sensors and the processor are integrated on a helmet for the skull.

7. The system of claim 1, wherein the sensors comprise at least one of acoustic transducers, accelerometers, or optical sound sensors.

8. The system of claim 1, wherein the sensors include acoustic transducers of an acoustic transducer array, and the processor is configured to control the acoustic transducer array to apply ultrasound energy to the brain to suppress the seizure.

9. The system of claim 8, wherein the ultrasound energy has a frequency in a range from 0.5 megahertz to 5 megahertz.

10. The system of claim 1, wherein the sensors include acoustic transducers of an acoustic transducer array, and the processor is configured to control the acoustic transducer array to apply ultrasound energy to the source of the seizure in response to detecting the seizure.

11. The system of claim 10, wherein the processor is configured to control the acoustic transducer array to apply the ultrasound energy within a millisecond time range from receiving the output signals from the sensors.

12. A method of detecting seizures from acoustic waves, the method comprising:

sensing, with sensors positioned outside of a skull encasing a brain, acoustic waves associated with neural activity of the brain, wherein the acoustic waves comprise compressional waves having a wavelength on the order of a meter; and detecting, with a processor in communication with the sensors, a seizure based on output signals of the sensors.

13. The method of claim 12, wherein the acoustic waves further comprise shear waves.

14. The method of claim 12, further comprising localizing a source of the seizure with millimeter scale resolution.

15. The method of claim 14, further comprising applying ultrasound energy to the source of the seizure in response to detecting the seizure.

16. The method of claim 15, wherein the ultrasound energy has a frequency in a range from 0.5 megahertz to 5 megahertz.

17. The method of claim 15, wherein the applying the ultrasound energy is performed within a millisecond time range from receiving the output signals of the sensors.

18. A method of detecting and suppressing seizures, the method comprising:

sensing, with sensors positioned outside of a skull encasing a brain, acoustic waves associated with neural activity of the brain at a plurality of locations;

comparing, with a processor in communication with the sensors, data derived using the sensors with a model associated with the skull;

based on the comparing, determining a location of the neural activity of the brain with a resolution on the order of a millimeter; and applying, using one or more ultrasonic transducers, ultrasound energy to the location of the neural activity in the brain through the skull within a millisecond time range from the determining.

19. The method of claim 18, wherein the acoustic waves comprise shear waves.

20. The method of claim 18, wherein the acoustic waves comprise compressional waves having a wavelength on the order of a meter.

* * * * *